(12) United States Patent
Sieber et al.

(10) Patent No.: US 7,205,002 B2
(45) Date of Patent: Apr. 17, 2007

(54) METHOD OF MAKING, AND THE USE OF CYTOTOXIC AGENTS CONTAINING ELEMENTAL SELENIUM

(75) Inventors: Fritz Sieber, Brookfield, WI (US); Wolfgang H. H. Günther, West Chester, PA (US); Jean-Pierre Daziano, Marseilles (FR); Marianne Krieg-Kowald, Barrington, RI (US); Jamal Bousbaa, Durham (GB); Raymond J. Bula, Cross Plains, WI (US)

(73) Assignee: MCW Research Foundation, Inc., Milwaukee, WI (US)

( * ) Notice: Subject to any disclaimer, the term of this patent is extended or adjusted under 35 U.S.C. 154(b) by 67 days.

(21) Appl. No.: 10/701,870

(22) Filed: Nov. 5, 2003

(65) Prior Publication Data

US 2005/0053675 A1 Mar. 10, 2005

Related U.S. Application Data

(60) Provisional application No. 60/424,354, filed on Nov. 6, 2002.

(51) Int. Cl.
*A61K 33/04* (2006.01)
*A61K 38/38* (2006.01)

(52) U.S. Cl. .......................... 424/702; 514/6
(58) Field of Classification Search ................ 436/525; 544/300; 424/702; 514/6
See application file for complete search history.

(56) References Cited

U.S. PATENT DOCUMENTS

| 5,091,385 A | 2/1992 | Gulliya et al. |
| 6,033,917 A | 3/2000 | Spallholz et al. |
| 6,416,782 B1 | 7/2002 | Maas |

OTHER PUBLICATIONS

Zhang, J.S., et al. 2001. Biological effects of a nano red elemental selenium. Biofactors 15: 27-38.*
Kuchan, M.J., et al. 1992 Cancer Research 52: 1091-1095.*
Labrenz, M., et al. 2000 Science 290(5497): 1744-1747.*
Lou, S.C., et al. 1993 Clinical Chemistry 39(4): 619-624.*
Günther WHH, Searle R. and Sieber F; Structure-Activity Relationships in the Antiviral and Antileukemic Photoproperties of Merocyanine Dyes; Seminars in Hematology, vol. 29, No. 2, pp. 88-94, 1992.
Günther WHH, Searle R and Sieber F; Photosensitizing Merocyanine Dyes Based on Selenobarbituric Acid; Phosphorus, Sulfur, and Silicon, vol. 67: pp. 417-424, 1992.
Krieg M, Bilitz JM, Traul DL and Sieber F; Photosensitizing Oxonol Dyes with Antineoplastic Activity, Cancer Research, Therapy and Control, vol. 4, pp. 163-172, 1995.
Burger AM, Hartung G, Stehle G, Sinn H, Fiebig HH: Pre-Clinical Evaluation of a Methotrexate-Albumin Conjugate (MTX-HSA) in Human Tumor Xenografts In Vivo; Int. J. Cancer: 92, 718-724, 2001.

(Continued)

*Primary Examiner*—Kathleeen M. Kerr
*Assistant Examiner*—Marsha Tsay
(74) *Attorney, Agent, or Firm*—Quarles & Brady LLP

(57) ABSTRACT

Pharmaceutical compositions containing elemental selenium (Se(0)), Se(0)-carrier conjugates, a chromophore photoproduct, fluorescent conjugates of the chromophore photoproduct and carrier molecules, or a mixture thereof are disclosed. Methods of using the pharmaceutical compositions such as inducing cell death are also disclosed. Further disclosed are methods of making the pharmaceutical compositions and components thereof.

17 Claims, 31 Drawing Sheets

OTHER PUBLICATIONS

Wunder A, Müller-Ladner U, Stelzer EHK, Funk J., Neumann E, Stehle G, Pap T, Sinn H, Gay S, Fiehn C; Albumin-Based Drug Delivery as Novel Therapeutic Approach for Rheumatoid Arthritis; The Journal of Immunology, 170, 4793-4801, 2003.

Yan L, Yee JA, Boylan LM, Spallholz JE; Effect of Selenium Compounds and Thiols on Human Mammary Tumor Cells, Biological Trace Element Research, vol. 30, pp. 145-162, 1991.

Zhang J-S, Gao X-Y, Zhang L-D, Bao Y-P; Biological effects of a nano red elemental selenium, BioFactors 16, 27-38, 2001.

Huang B, Zhang J, Hou J, Chen C; Free Radical Scavenging Efficiency of Nano-Se In Vitro; Free Radical Biology & Medicine, vol. 35, No. 7, pp. 805-813, 2003.

Sieber F, Daziano J-P, Anderson GS, Miyagi K, Sampson RW, Tsujino I, Günther WHH, Krieg M, Bousbaa J and Försterling FH; Collodial Selenium Generated by Photobleaching of Selenomerocyanine Dyes Combines with Serum Macromolecules to Form Conjugates that are Preferentially Cytotoxic to Leukemia and Selected Solid Tumor Cells: Blood 100. 224b. 2002.

Miyagi K, Sampson RW, Tsujino I, Gunther WHH, Krieg M and Sieber F; Proteinated subnanoparticles of elemental selenium potentiate the anti-tumor effect of ionizing radiation and selected chemotherapeutic agents; Proceedings of the American Association Cancer Research, vol. 44, 385, 2003.

Sieber F; Proteinated Subnanoparticles of Colloidal Selenium: A New Class of Anti-Leukemia/Lymphoma Agents; Leukemia 17: 683, 2003.

Oral Presentation at 32nd Annual Scientific Meeting of the International Society for Experimental Hematology, Paris (France), Jul. 7, 203.

G. S. Anderson, et al., "Inactivation of Photosensitizing Merocyanine Dyes by Plasma, Serum and Serum Components," Photochem. Photobiol. 64(4):683-687, 1996.

* cited by examiner

METHOD OF MAKING, AND THE USE OF CYTOTOXIC AGENTS CONTAINING ELEMENTAL SELENIUM

CROSS-REFERENCE TO RELATED APPLICATIONS

This application claims the benefit of U.S. provisional application Ser. No. 60/424,354, filed on Nov. 6, 2002.

STATEMENT REGARDING FEDERALLY SPONSORED RESEARCH OR DEVELOPMENT

This invention was made with United States government support awarded by the following agency: National Cancer Institute, Grant Number RO1-CA77387. The United States has certain rights in this invention.

BACKGROUND OF THE INVENTION

The effect of selenium compounds on biological systems has been of great interest to researchers. Although selenium is toxic if taken in high doses, it is an essential trace element in a healthy diet. Various selenium-based compounds, such as selenium sulfides, have long been recognized for therapeutic applications in the topical treatments for dandruff, eczemas and dermatomycoses. Researchers have also explored the use of selenium based compounds in nutritional supplements for the protection of normal cells in the prevention of cancer, the inhibition of aging processes, and the replication of HIV in AIDS patients. More recently, research has focused on the use of selenium compounds as cytotoxic agents in the treatment of cancer.

Like most group VI elements, selenium occurs in different oxidation states (−II, 0, +II, +IV, and +VI). Up to now, all biologically active selenium compounds were derived from selenium in oxidation states −II, +II, +IV, or +VI. Selenium having an oxidation state zero (Se(0)) however, was believed to be biologically inert.

BRIEF SUMMARY OF THE INVENTION

In one aspect, the present invention relates to a pharmaceutical composition that contains elemental selenium (Se(0)) particles and a pharmaceutically acceptable delivering medium. The composition can further contain a carrier molecule that has the capability of being internalized by a living cell through endocytosis or other mechanisms and the capability of forming a conjugate with one or more Se(0) particles in the composition.

In another aspect, the present invention relates to a method of causing a cell to die, a method of reducing intracellular glutathione, and a method of sensitizing a cell to cytotoxic agents that the cell is resistant to due to the presence of intracellular glutathione. All these methods involve introducing Se(0) particles into a target cell using the compositions of the present invention. In various embodiments of the methods, Se(0) is introduced into target cells for treating cancer, for extracorporeal purging of autologous hematopoietic stem cell grafts, for removing alloreactive lymphocytes from allogeneic stem cell grafts, for treating parasitic infection in a human or nonhuman animal, for inactivating parasites and parasitized blood cells in blood or a blood product, for treating autoimmune disorders or graft-versus-host diseases.

In another aspect, the present invention relates to a pharmaceutical composition that contains fluorescent chromophore photoproduct-carrier conjugates made by a photochemical method described below and a pharmaceutically acceptable delivering medium. The fluorescent conjugates can be used along with the Se(0)-carrier conjugates having the same carrier molecule to trace the entering and the amount of Se(0) that enters into a target cell. The fluorescent conjugates are also useful in pharmacokinetic studies, tissue distribution studies of Se(0)-carrier conjugates, and identification of Se(0)-carrier conjugate sensitive target cells. In addition, the fluorescent conjugates can be used as a diagnostic tool for a disease such as cancer wherein the disease cells internalize more carrier molecules than normal cells.

In another aspect, the present invention relates to a photochemical method for generating Se(0), Se(0)-carrier conjugates, a chromophore photoproduct, or fluorescent conjugates of the chromophore photoproduct and carrier molecules. The method involves providing a suitable starting dye, exposing the dye to light of a suitable wavelength in the presence of molecular oxygen to form Se(0) or a chromophore photoproduct, and purifying Se(0) or the chromophore photoproduct. For generating a Se(0)-carrier conjugate or a fluorescent conjugate of the chromophore photoproduct and carrier molecules, carrier molecules can be mixed with the dye before, at the same time or after the dye is exposed to the light and oxygen. The conjugates formed can then be purified. When suitable starting dyes are used, Se(0)-carrier conjugates and the fluorescent conjugates can be generated from the same dye.

In another aspect, the present invention relates to a chemical method of generating Se(0)-carrier conjugates. The method involves reducing selenium dioxide, selenious acid or selenite salts in the presence of carrier molecules.

It is an advantageous of the present invention that carrier molecules specific for a target cell can be selected for forming Se(0)-carrier conjugates so that the conjugates have target specificity.

Other objects, features and advantages of the present invention will be apparent from the following detailed description when taken in conjunction with the accompanying claims and drawings.

BRIEF DESCRIPTION OF THE SEVERAL VIEWS OF THE DRAWINGS

In FIG. 12, the "Z-" prefix and the "-FMK" suffix are omitted because of space limitations.

DETAILED DESCRIPTION OF THE INVENTION

Figure 1:
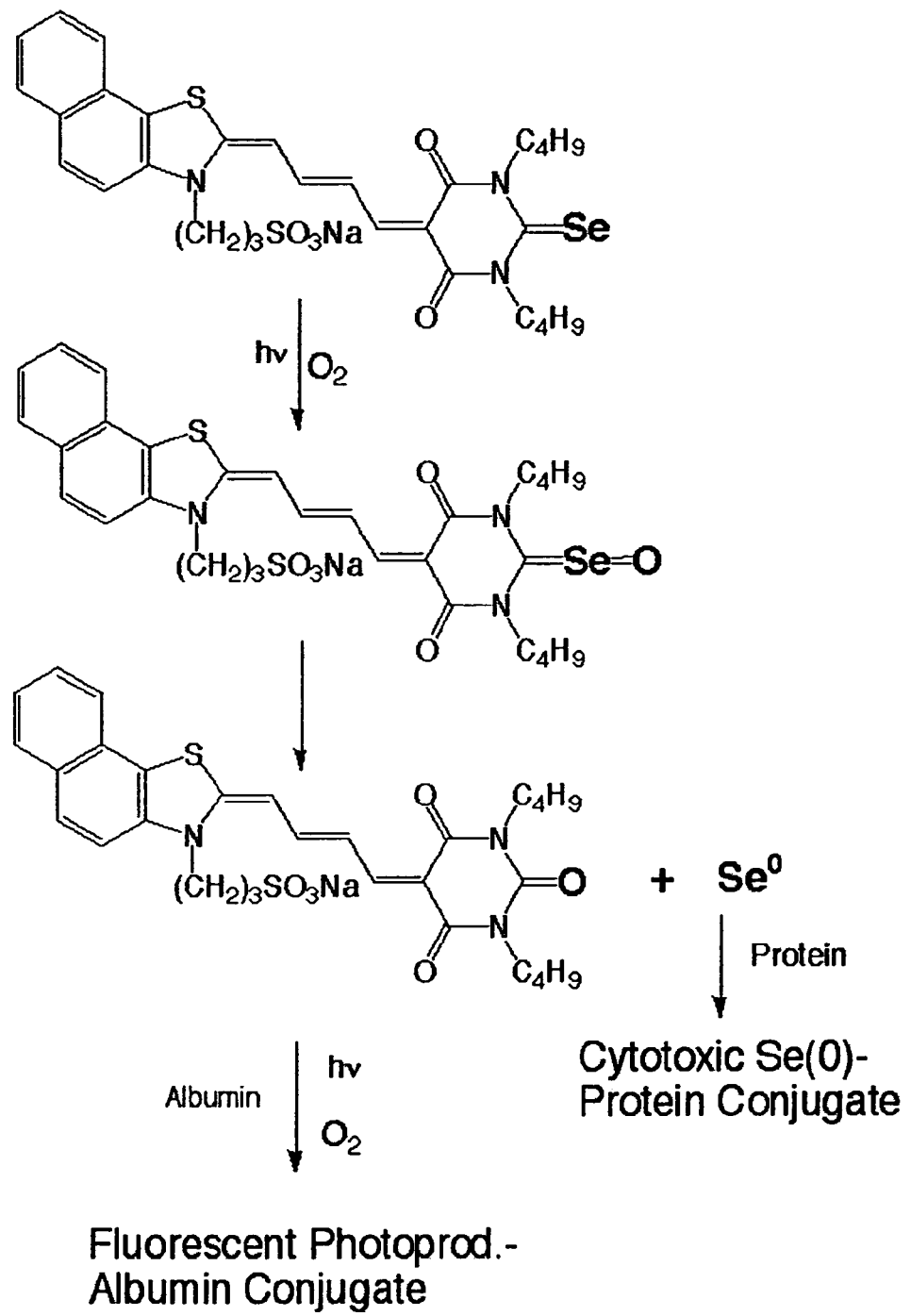
FIG. 1 shows a proposed reaction scheme for photochemical generation of cytotoxic/fluorescent conjugates.

It is disclosed herein that selenium in oxidation state 0 (elemental selenium or Se(0)) has cytotoxic activity when introduced into cells. It is further disclosed that introducing Se(0) into cells that are resistant to certain cytotoxic agents (e.g., ionizing radiation and alkylating agents) due to the presence of intracellular glutathione can sensitize these cells to the cytotoxic agents. As described in the examples below, Se(0) catalyzes the oxidation of intracellular thiols upon entering into the cells. Without intending to be limited by theory, the inventors believe that the cytotoxic activity of Se(0) relates to the depletion of reduced thiols, the accumulation of oxidized thiols or both, and the cell-sensitizing activity of Se(0) relates to the depletion of reduced thiols.

In one aspect, the present invention relates to a pharmaceutical composition that contains Se(0) particles and a pharmaceutically acceptable delivering medium. The composition can further contain a carrier molecule that forms a conjugate with one or more Se(0) particles in the composition. The term "carrier molecule" as used in the specification and claims refers to a molecule that has the capability of forming a conjugate with Se(0) and the capability of entering into a target cell through endocytosis or other mechanisms. Therefore, the carrier molecule can serve as a vehicle for introducing Se(0) into a target cell by forming a conjugate with Se(0). It is well within the capability of a skilled artisan to identify suitable carrier molecules for various target cells. Examples of such carrier molecules include but are not limited to proteins, glycoproteins and lipoproteins. Some specific examples of suitable carrier molecules include but are not limited to albumin, high density lipoprotein (HDL), low density lipoprotein (LDL), very low density lipoprotein (VLDL) and antibodies for certain cell surface molecules of a target cell. A carrier molecule does not have to be a naturally-occurring molecule. For example, albumin is a suitable carrier for many types of cancer cells. It is appreciated that certain modifications on a naturally-occurring albumin molecule will not abolish its Se(0)-conjugating and cell-entering capabilities and these modified albumin molecules are suitable carrier molecules.

A pharmaceutically acceptable delivering medium is a medium that is suitable for ex vivo treatment of a cell sample that will be later introduced back to a human or nonhuman animal or a medium that can be administered to human or nonhuman animal. A skilled artisan is familiar with such a medium. The term "pharmaceutically acceptable delivering medium" is synonymous to the term "pharmaceutically acceptable carrier" that is also frequently used in the art. However, the term "pharmaceutically acceptable carrier" is avoided in the specification and claims to avoid any confusion with the carrier molecules that are used for forming conjugates with Se(0). Any of the standard pharmaceutically acceptable delivering media known to those of ordinary skill in the art can be used in the composition of the present invention. Examples of such standard delivering media include, but are not limited to, phosphate buffered saline solution, water, emulsions such as oil/water emulsions or a triglyceride emulsion, various types of wetting agents, tablets, coated tablets and capsules. A suitable pharmaceutically accepted medium may be selected taking into account the chosen mode of administration. For example, depending on the specific applications, the composition of the present invention may be administered systemically or locally (e.g., intravenously, intraperitoneally, parenterally, orally, topically, injected into tumor tissue). Specifically excluded from the definition of a pharmaceutically acceptable medium is the mixture at the end of a photochemical reaction for generating Se(0)-carrier conjugates or chromophore photoproduct-carrier conjugates minus the Se(0)-carrier conjugates or chromophore photoproduct-carrier conjugates contained therein. Photochemical reactions for generating Se(0)-carrier conjugates or chromophore photoproduct-carrier conjugates are described below.

Preferably, Se(0) particles in the present invention form a Se(0) colloid in a dispersion medium such as a pharmaceutically acceptable liquid delivering medium. Typically, colloidal Se(0) particles have a diameter of 0.4 to 50 nanometers, 0.4 to 5 nanometers, or 0.4 to 1 nanometer.

In another aspect, the present invention relates to a method of causing a cell to die, a method of reducing intracellular glutathione, and a method of sensitizing a cell to cytotoxic agents that the cell is resistant to due to the presence of intracellular glutathione. All these methods involve introducing Se(0) particles into a target cell using the compositions of the present invention. Preferably, the Se(0) particles introduced into the target cell are of a size that allows the formation of a Se(0) colloid when suspended in a pharmaceutically acceptable medium.

There are many ways that Se(0) can be introduced into a target cell and any of them can be used in the present invention. In one embodiment, Se(0) is introduced into a target cell via a suitable carrier molecule by forming a conjugate with the carrier molecule. Se(0)-carrier conjugates can be generated by mixing carrier molecules with Se(0), preferably colloidal Se(0). Se(0) or colloidal Se(0) can be obtained from a commercial source or generated by a method known to a skilled artisan. Examples of photochemical methods and chemical methods for forming colloidal Se(0) and Se(0)-carrier conjugates are described below as other aspects of the present invention.

Figure 2:
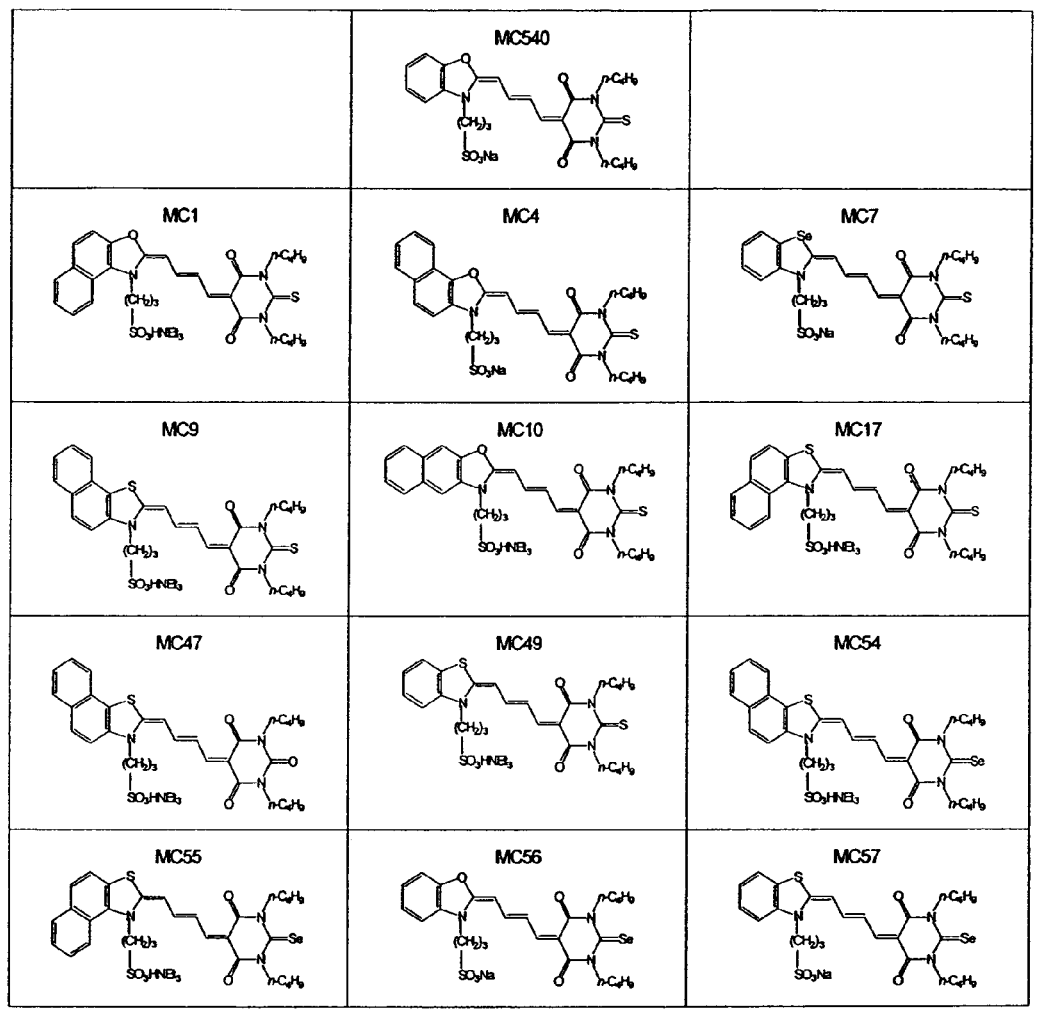
FIG. 2 shows structures of selected merocyanine dyes.

In another aspect, the present invention is a photochemical method of making colloidal Se(0) and Se(0)-carrier conjugates. The method involves exposing a photosensitizing selone dye to light of a suitable wavelength in the presence of molecular oxygen (photobleaching). Examples of selone dyes that can be used include selenomerocyanine and selenooxonol dyes. Selenomerocyanine dyes and selenooxonol dyes are described in (1) U.S. Pat. No. 5,208,336, (2) Günther, W. H. H. et al., Abstracts, $6^{th}$ International Conference on the Chemistry of Selenium and Tellurium, Osaka, Japan, OP-11, p. 27 (1991), (3) Günther, W. H. H. et al., Abstracts, $20^{th}$ Annual Meeting of the International Society for Experimental Hematology, Parma, Italy, Jul. 21–26, 1991, and (4) Krieg, M. et al., Cancer Research, Therapy and Control, 4: 163–172, 1995, all of which are herein incorporated by reference in their entirety. As described in the examples below, a Se in the 2-position of the barbiturate of a photosensitizing selone dye is essential for the generation of Se(0) by the photochemical process. The Se(0) formed from this process is in colloidal form. For generating Se(0)-carrier conjugates, carrier molecules can be mixed with the dye before, at the same time, or after the dye is exposed to the light. Examples of suitable selenomerocyanine dyes that can be used to generate colloidal Se(0) and Se(0)-carrier conjugates include but are not limited to MC54, MC55, MC56 and MC57 as illustrated in FIG. 2. A mechanism of how Se(0) is formed from the dyes is illustrated in FIG. 1. A selenooxonol dye contains two selenium groups that can be extracted to form Se(0) and is twice as efficient as a selenomerocyanine dye for generating Se(0).

A suitable light source for the photochemical method of the present invention is one that emits light with a spectrum that adequately overlaps with the absorption spectrum of a starting photosensitizing dye. The suitable wavelengths and suitable light sources are either known to or can readily be determined by a skilled artisan. For example, broad-spectrum light sources such as white fluorescent light are suitable light sources.

The cytotoxic activity of Se(0)-carrier conjugates can be modulated by altering the Se(0):carrier ratio of the conjugates. Conjugates with a high Se(0):carrier ratio are more toxic than conjugates with a low Se(0):carrier ratio.

Colloidal Se(0) and Se(0)-carrier conjugates formed by the photochemical method can be purified from the mixture at the end of the photochemical reaction. Purification of colloidal Se(0) and Se(0)-carrier conjugates encompass either partial or complete purification. Removal of any non-Se(0) and non-Se(0)-carrier conjugates component of the reaction mixture is considered a partial purification. A skilled artisan is familiar with the purification methods that can be used. For example, as shown in FIG. 1, reaction products that contain a soluble sulfonic acid anion can form during the photobleaching process when MC54, MC55 or MC57 is used as the starting dye. These soluble products can be removed by using an insoluble reagent that contains suitable cationic centers to convert the soluble products into insoluble salt products through ion exchange. The insoluble products can then be removed through filtration. Alternatively, the photochemical reaction mixture can be passed through a column packed with a cationic reagent. Cationic ion exchange resins that can be used in the purification method are commercially available from Sigma-Aldrich.

A size-based method can also be used to purify Se(0)-carrier conjugates. Se(0)-carrier conjugates are larger than various dye fragments formed at the end of the photochemical reaction. Thus, the reaction mixture can be partially purified through gel filtration, ultrafiltration or dialysis. In addition, affinity chromatography and hydrophobic interaction chromatography can be used to purify the Se(0)-carrier conjugates. Affinity chromatography takes advantage of materials that have specific affinity for a carrier molecule. For example, affi-gel blue and certain antibodies bind rather specifically to albumin. When albumin is used as the carrier molecule, a matrix derivatized with cibacron blue or anti-albumin antibodies can be used to purify Se(0)-albumin conjugates. Hydrophobic interaction chromatography takes advantage of hydrophobicity differences between Se(0)-carrier conjugates and various dye fragments so that they have different retention time when eluted by a suitable solution.

In another aspect, the present invention is a chemical method for generating Se(0)-carrier conjugates. If chemical reactions for generating Se(0) are carried out in the presence of a carrier, Se(0)-carrier conjugates can be formed. Alternatively, the carrier can be added after Se(0) is generated to form Se(0)-carrier conjugates. The Se(0)-carrier conjugates can be purified using some of the purification methods described above. Examples of chemical methods for generating colloidal Se(0) is shown in Table 3.

In another aspect, the present invention relates to a photochemical method of making a chromophore photoproduct and a fluorescent conjugate of the chromophore photoproduct and a carrier molecule. The method involves exposing a merocyanine dye that contains a sulfur or a selenium atom in the donor heterocycle to light of a suitable wavelength in the presence of molecular oxygen to generate a chromophore photoproduct. For generating the fluorescent conjugate, a carrier molecule is added to the dye before, at the same time or after the dye is exposed to the light. The emission spectrum of the light source has to show adequate overlap with the absorption spectrum of the merocyanine dye and any intermediate analogue of the dye that leads to the formation of the chromophore photoproduct. Although broad-spectrum light may be used, it is not preferred because overlap between the emission spectrum of the light source and the absorption spectrum of the fluorescent conjugates can cause bleaching of the fluorescent conjugates. Bleaching of fluorescent conjugates can be minimized by filters that eliminate the undesirable portions of the visible spectrum, or, more preferably, by the use of light-emitting diodes (LED) with a narrow-band emission spectrum.

Examples of suitable merocyanine dyes that can be used to generate a chromophore photoproduct and a fluorescent conjugate of the chromophore photoproduct and a carrier include but are not limited to MC7, MC9, MC17, MC49, MC54, MC55 and MC57 as illustrated in FIG. 2. A mechanism of the photochemical method is illustrated in FIG. 1.

A carrier molecule suitable for the method of generating a fluorescent conjugate with a chromophore photoproduct is one that has the capability of entering into a target cell through endocytosis or other mechanisms and the capability of forming a fluorescent conjugate with the chromophore photoproduct. Suitable carrier molecules are not limited to naturally occurring molecules. The examples below show that albumin is a suitable carrier molecule and other suitable carrier molecules can be readily screened and identified by a skilled artisan.

It is noted that Se(0)-carrier conjugates and fluorescent conjugates of a chromophore photoproduct and a carrier molecule can be made from a common selenomerocyanine dye in a single process. The common selenomerocyanine must contain a sulfur or a selenium atom in the donor heterocycle. Examples of such selenomerocyanine dyes include but are not limited to MC54, MC55 and MC57. A proposed mechanism for such a process is illustrated in FIG. 1.

The fluorescent conjugates can be purified from the mixture at the end of a photochemical reaction using a size-based method, affinity chromatography or hydrophobic interaction chromatography as described above for purifying Se(0)-carrier conjugates.

In another aspect, the present invention relates to a pharmaceutical composition that contains partially or completely purified fluorescent conjugates as described above and a pharmaceutically acceptable delivering medium.

The fluorescent conjugates can be used along with Se(0)-carrier conjugates having the same carrier molecule to trace the entering and the amount of Se(0) that enters into a target cell. In this regard, using MC54, MC55 and MC57 is advantageous because photobleaching these dyes will generate a composition that contains both the Se(0)-carrier conjugates and the fluorescent photoproduct-carrier conjugates.

The fluorescent conjugates are also useful in pharmacokinetic studies, tissue distribution studies of Se(0)-carrier conjugates, and identification of Se(0)-carrier conjugate sensitive target cells.

The fluorescent conjugates can also be used as a diagnostic tool for a disease if the disease cells can internalize more carrier molecules than normal cells. For example, many cancer cells internalize more albumin than normal cells. Fluorescent conjugates with albumin as the carrier can thus be used to diagnose cancer. For example, one can administer the conjugates to a patient (either systematically or locally) and analyze the fluorescent level of cells obtained from tissues that are suspected of cancer. If the cells have a higher fluorescence level than surrounding cells or a normal level otherwise established, the cells are likely to be cancerous. This process can also help identifying residual tumor cells in vicinity of a solid tumor to provide guidance during surgical resection. Micrometastases can also be detected similarly. In another embodiment, identification of tumor cells in peripheral blood or autologous stem cell grafts can be made by either intravenous injection of the fluorescent conjugates or exposing a blood sample to the fluorescent conjugates ex vivo.

The cytotoxic and thiol depletion activities of Se(0) and the Se(0)-carrier conjugates disclosed here have a broad range of applications. One application is a method of treating cancers in a human or nonhuman animal by introducing Se(0), preferably colloidal Se(0), into cancer cells. In one embodiment, Se(0) is introduced into cancer cells by treating a human or nonhuman animal with a composition that contains Se(0) or Se(0)-carrier conjugates and a pharmaceutically acceptable delivering medium. An example of the carrier molecules that can be used is albumin. Serum albumin is known to play a key role in the energy and nitrogen metabolism of many tumor cells. More than 90% of carcinomas overexpress the albumin receptor and internalize and metabolize albumin at a higher rate than normal cells. Albumin can access the interstitial space by leaving the vascular system via transcytosis. While the interstitial pressure in solid tumors represents a major obstacle to the delivery of standard drugs, interstitial pressure does not prevent the accumulation of albumin in tumor tissue. In addition, albumin has a long half-life (approximately 19 days). During its life time, albumin passes about 15,000 times through the circulatory system and 15 times through the extravascular space. In addition, albumin does not accumulate in adrenals, liver and bone marrow. Albumin-drug conjugates are therefore, well suited to maintain relatively constant drug levels. Another example of the carrier molecules that can be used is LDL. LDL targets certain tumors even more specifically than albumin. Melanomas, for example, accumulate 28 times more LDL than the corresponding normal tissues. When LDL is used as a carrier for Se(0), one should keep in mind that unlike albumin, LDL also accumulates in adrenals, liver and bone marrow.

A composition that contains Se(0) or Se(0)-carrier conjugates and a pharmaceutically acceptable delivering medium can be administered to a human or nonhuman animal via different modes. For example, the composition can be injected intravenously for systemic treatment. For tumors that tend to form ascites in the peritoneal cavity (e.g., ovarian cancer), intraperitoneal injection may be preferred. The composition can also be injected to a tumor or tissues immediately adjacent to the tumor for local treatment.

A major concern in cancer therapy is the emergence of drug-resistant tumor cells. Elevating the concentration of intracellular glutathione is one mechanism by which cancer cells become resistant to therapy. Se(0)-carrier conjugates can restore the sensitivity of these cancer cells to standard chemotherapeutic agents. Unlike agents that interfere with the biosynthesis of glutathione, Se(0)-carrier conjugates are fast-acting. In tissue culture models, Se(0)-carrier conjugates typically reduced intracellular glutathione levels by 50% to 75% in as little as one hour. By contrast, inhibitors of glutathione biosynthesis typically required at least 15 hours to achieve a 50% reduction of glutathione.

In another application, Se(0) is used for extracorporeal purging of autologous hematopoietic stem cell grafts (ex vivo purging). In one embodiment, Se(0) is introduced into stem cells by treating the stem cells ex vivo with a pharmaceutical composition containing Se(0)-carrier (e.g., albumin) conjugates and a pharmaceutically acceptable delivering medium. For example, the mononuclear fraction of a blood or bone marrow sample can be suspended at a density of $10^6$ to $10^7$ per ml in an isotonic medium (e.g., alpha-modified Dulbecco's medium) that is supplemented with a suitable concentration of Se(0)-albumin conjugates (e.g., 10–20 µM). The cell suspension is then incubated at 37° C. for about one hour, washed free of excess conjugates, and cryopreserved until needed for reinfusion into a patient.

In another application, Se(0) is used to remove alloreactive lymphocytes from allogeneic stem cell grafts in a manner similarly to that of ex vivo purging of autologous hematopoietic stem cell grafts. In another application, the ex vivo process is used to inactivate parasites and parasitized blood cells in blood or a blood product. However, for treating parasitic infection in a human or nonhuman animal, a Se(0)-containing agent should be administered to the human or nonhuman animal intravenously. In one embodiment, the Se(0)-containing agent is a composition that contains Se(0)-carrier conjugates and a pharmaceutically acceptable delivering medium.

In another application, Se(0) is introduced into immune cells that are responsible for an autoimmune disorder or graft-versus-host disease to kill these immune cells. In one embodiment, a composition containing Se(0)-carrier conjugates and a pharmaceutically acceptable delivering medium is injected intravenously into a patient suffering from the disorder or disease. For treating an autoimmune disease, the composition may be administered locally as well.

The invention will be more fully understood upon consideration of the following non-limiting examples. In the following examples, all references to molar concentrations of Se(0)-protein conjugates refer to the molar concentration of the selenium component.

EXAMPLE 1

Purification and Characterization of Photoproduct-Protein Conjugates

In this example, we describe the determination of the structure of photoproducts and photoproduct protein conjugates and the elucidation of the reaction pathways that lead to their formation during the photobleaching of selenomerocyanine photosensitizers. FIG. 1 summarizes our current understanding of the reaction pathways for the formation of cytotoxic and fluorescent photoproduct-protein conjugates. The experimental evidence in support of the proposed scheme is summarized below.

Materials and Methods

Determining the fluorescence emission spectrum of photoproduct-albumin conjugates: Photoproduct-albumin conjugates were generated by adding selenomerocyanine dye MC54 from a 67-fold concentrated stock solution in ethanol to a 20 µM solution of bovine serum albumin in 10 mM HEPES buffer pH 7.4. Two-ml aliquots of the solution were placed into clear 15-ml polybutadiene styrene tubes (the large air space above the solution insured an adequate supply of oxygen) that were mounted on a rotating (30 rpm) plexiglas disk between two panels of cool-white tubular fluorescent lights (5 tubes per panel) and irradiated for 60 minutes. The fluence rate at the sample site was 27 W/m² as determined by a model 351A power meter equipped with a model 262 detector (United Detector, Hawthorne, Calif.) The reaction product was diluted 30-fold with 10 mM HEPES buffer pH 7.4, and a fluorescence emission spectrum was recorded with a Hitachi F-4500 fluorescence spectrophotometer using an excitation wavelength of 490 nm (HEPES: 4-(2-hydroxyethyl)-1-piperazineethanesulfonic acid hemi sodium salt).

Optimal dye:protein ratios for generation of fluorescent and cytotoxic conjugates: Bovine serum albumin was dissolved at a concentration of 1.75 mg/ml in 10 mM HEPES buffer pH 7.4. Selenomerocyanine dye MC54 was added from a 1.75 mM stock solution in ethanol to achieve dye:protein molar ratios of between 0.25:1 and 5:1. The mixtures were exposed to white light (27 W/m²) for 60 min as deescribed above. To assess fluorescent conjugate formation, the photoirradiated mixtures were diluted 30 times with 10 mM HEPES buffer pH 7.4, and fluorescence emission spectra were recorded with a Hitachi F-4500 fluorescence spectrophotometer using an excitation wavelength of 490 nm. To assess cytotoxic activity, cytotoxic conjugates were made isotonic by the addition of an appropriate volume of double-concentrated alpha-medium and incubated with L1210 leukemia cells for 60 min at 37° C. The surviving fraction of in vitro clonogenic leukemia cells was determined by in vitro clonal assay as described in Sieber, F. et al., 1984, which is incorporated by reference in its entirety.

Results and Discussion

Structure-Activity Relationships: Extended structure-activity studies (FIG. 2, Table 1) showed that cytotoxicity and fluorescence activity were independently regulated (the structures in FIG. 2 were synthesized as described in Günther, W. H. H. et al., 1992, which is herein incorporated by reference in its entirety). All selenobarbituric acid analogues but none of the thiobarbituric or barbituric acid analogues formed cytotoxic conjugates. This indicated that the selone group was essential for the formation of cytotoxic conjugates. A quantitative comparison of the potencies of conjugates generated by four selenomerocyanine dyes and one selenooxonol dye (Krieg, M. et al., 1995) showed that cytotoxic activity was not a function of singlet oxygen quantum yields but a function of the number of selone groups per dye molecule. The selenooxonol dye with its 2 selone groups could generate two Se(0) atoms. Selenomerocyanines with their single selone groups could only generate one Se(0) atom. Conjugates generated by the oxonol dye were almost twice as cytotoxic as the ones generated by equimolar concentrations of merocyanine dyes. Fluorescent photoproduct-albumin conjugates were formed by all merocyanines dyes that contained a selenium or sulfur atom in the donor heterocycle (FIG. 2, Table 1).

TABLE 1

Structural Requirements for Formation of Fluorescent and Cytotoxic Conjugates by Photoproducts and Albumin

| Dye | Descriptor 1 | Descriptor 2 | Fluorescence | Cytotoxic Activity |
|---|---|---|---|---|
| MC1 | naphth[1,2-d]oxazole | thiobarbituric | no | no |
| MC4 | naphth[2,1-d]oxazole | thiobarbituric | no | no |
| MC49 | benzothiazole | hiobarbituric | yes | no |
| MC7 | benzoselenazole | thiobarbituric | yes | no |
| MC9 | naphth[2,1-d]thiazole | thiobarbituric | yes | no |
| MC17 | naphth[1,2-d]thiazole | thiobarbituric | yes | no |
| MC540 | benzoxazole | thiobarbituric | no | no |

TABLE 1-continued

Structural Requirements for Formation of Fluorescent and Cytotoxic Conjugates by Photoproducts and Albumin

| Dye | Descriptor 1 | Descriptor 2 | Fluorescence | Cytotoxic Activity |
|---|---|---|---|---|
| MC54 | naphth[2,1-d]thiazole | selenobarbituric | yes | yes |
| MC55 | naphth[1,2-d]thiazole | selenobarbituric | yes | yes |
| MC56 | benzoxazole | selenobarbituric | no | yes |
| MC57 | benzothiazole | selenobarbituric | yes | yes |
| Se-oxonol | selenobarbituric | selenobarbituric | no | yes |

Figure 3:
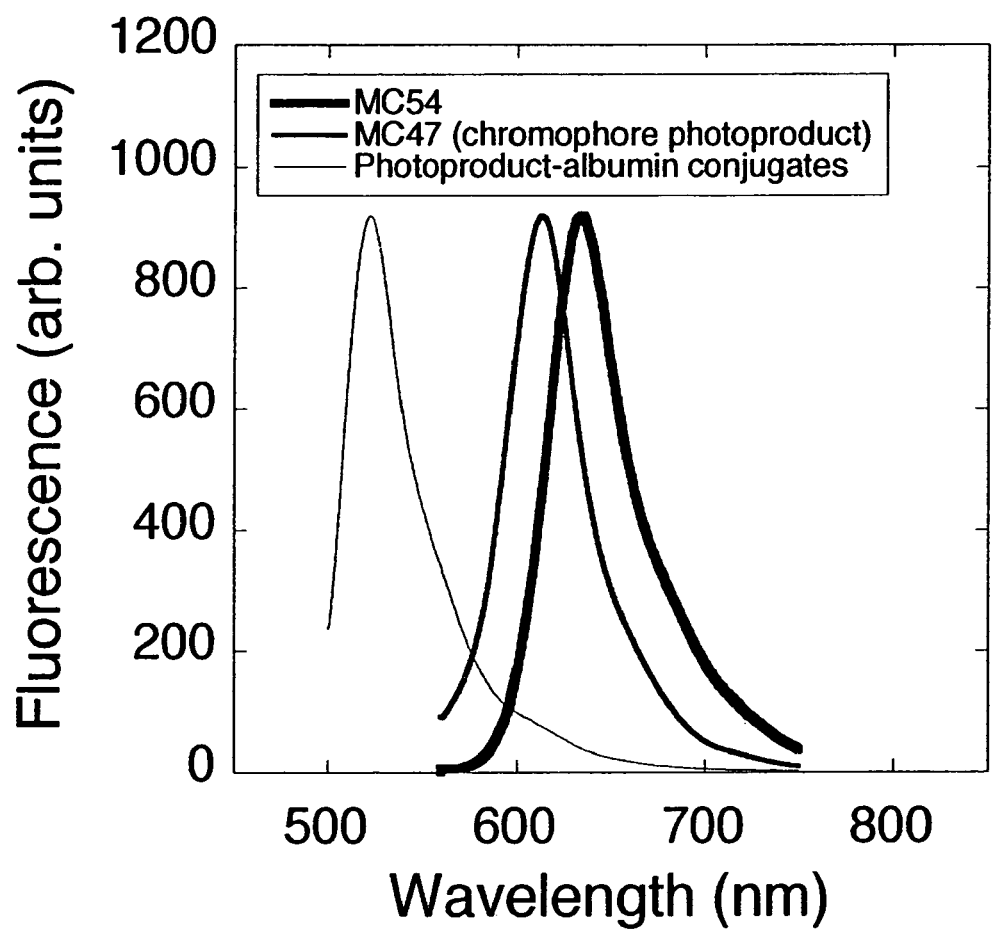
FIG. 3 shows normalized fluorescence emission spectra of MC54, photobleached MC54 (MC47) and MC54-derived photoproduct-albumin conjugates.
Figure 4:
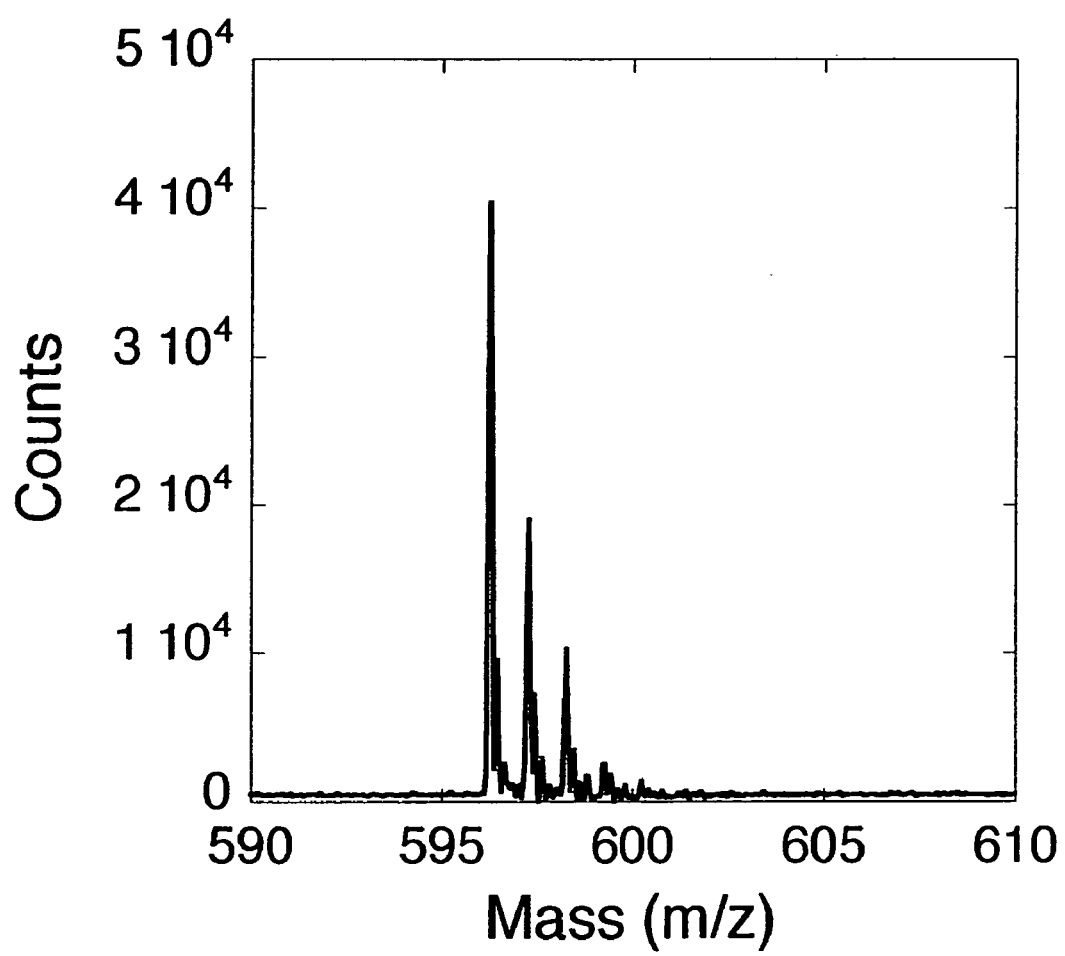
FIG. 4 shows mass spectrum of photobleached MC54. The observed mass of 596.25 agrees well with the calculated mass of 596.19.
Figure 5:
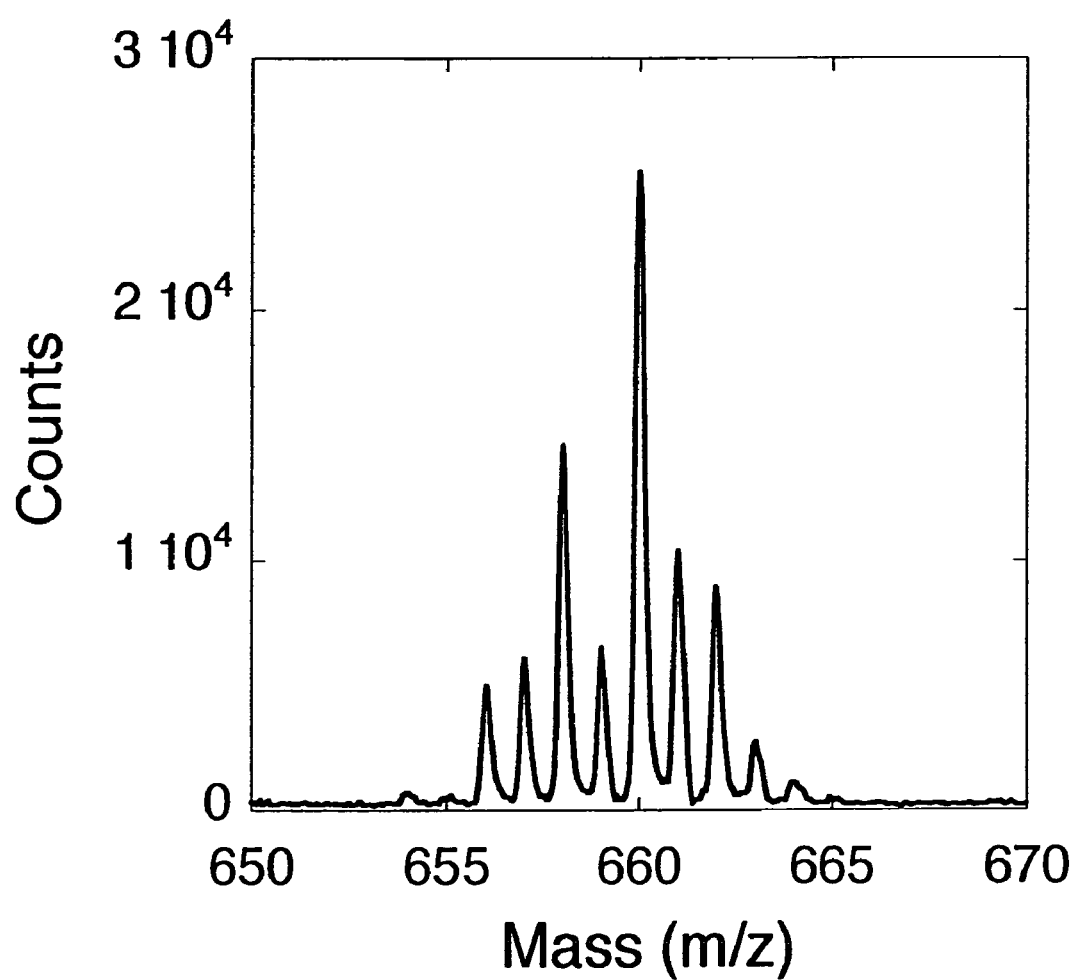
FIG. 5 shows mass spectrum of intact MC54 (characteristic isotope distribution of selenium).

Source of serum macromolecules: alpha-medium supplemented with 10% fetal bovine serum. Target cells for cytotoxicity assay: L1210 leukemia cells Reaction Pathways: The reaction scheme shown in FIG. 1 proposes an oxidation of the selone followed by a substitution of the selenium by an oxygen, the abscission of selenium zero, and the formation of a chromophore photoproduct that is identical with the barbituric acid analogue of the original selone dye (MC47, FIG. 2). The initial steps of the proposed scheme are supported by the following experimental evidence. (1) The absorption (not shown) and fluorescence emission (FIG. 3) spectra of the chromophore photoproduct were blue-shifted relative to the spectra of MC54 and indistinguishable the spectra of authentic MC47. (2) When the reaction was conducted in ethanol and in the absence of protein to prevent the formation of conjugates, sufficient quantities of the photoproduct (MC47) accumulated to allow purification on a silica column and subsequent characterization by thin layer chromatography, mass spectroscopy, and elemental analysis. Furthermore, a red deposit formed on the walls of the reaction vessel that was indicative of elemental selenium. Thin layer chromatograms of the chromophore photoproduct and authentic MC47 were indistinguishable. Mass spectroscopy performed on a Voyager System 6004 (PE Biosystems, Foster City, Calif.) MALDI-TOF (matrix-assisted laser desorption/ionization time of flight) mass spectrometer showed a mass of 596.3 (FIG. 4) for the isolated photoproduct, which agreed well with the calculated mass of 596.2 (mass of MC47 minus counter ion) of the proposed structure. The intact selone dye (MC54) showed the characteristic isotope distribution of selenium (FIG. 5). By contrast, neither the intact chromophore photoproduct nor any its fragments showed the characteristic isotope distribution of selenium. The elemental analysis (performed by Galbraith Laboratories, Knoxville, Tenn.) of the chromophore photoproduct was also consistent with the proposed structure.

Two corollaries of the proposed reaction scheme are that the production of photoproducts should be inhibited by quenchers of singlet oxygen or by a lack of molecular oxygen, and that one should be able to substitute other oxidants for singlet oxygen. The production of photoproducts and fluorescent/cytotoxic conjugates was indeed inhibited when oxygen in the buffer was replaced by argon, when the buffer was supplemented with azide or glutathione, or when dry ethanol was used instead of 90% ethanol (water in 90% ethanol serves as an oxygen donor). When MC54 was exposed to iodine, hydrogen peroxide, $Hg(CF_3CO_2)_2$, sodium hypochlorite, or chloramine T in the dark, the characteristic chromophore photoproduct (MC47) was formed as expected.

Binding of the chromophore photoproduct (MC47) to albumin required at least one additional oxidation step that was mediated by photogenerated singlet oxygen. Co-incubation of the purified photoproduct or of de-novo-synthesized MC47 with bovine serum albumin in a 1-to-1 molar ratio in the dark did not lead to the formation of green-fluorescent conjugates. Treatment of the chromophore photoproduct with chemical oxidants such as iodine, hydrogen peroxide, or $Hg(CF_3CO_2)_2$ did not lead to the formation of green-fluorescent conjugates either. However, when the purified photoproduct or the de-novo-synthesized MC47 were mixed in a 1-to-1 molar ratio with bovine serum albumin and exposed to cool white fluorescent light (fluence rate: 27 $W/m^2$), fluorescent photoproduct-albumin conjugates were readily formed as indicated by their characteristic excitation and fluorescence emission spectra.

We do not yet know why only dyes with a sulfur or selenium atom in the donor heterocycle formed fluorescent photoproduct albumin conjugates. One obvious difference between oxygen, sulfur and selenium is that only sulfur and selenium can be oxidized to oxidation states higher than II. Singlet oxygen is known to attack unsaturations in chromophores forming epoxides that may get internally rearranged to carbonyls. Either carbonyls or epoxides could react with amino groups of proteins. The oxazole dye may appear non-fluorescent because its spectrum is shifted too far to the blue for efficient excitation. Alternatively, it may be non-fluorescent because the oxazole ring hydrolyzes to a hydroxyamide, thereby interrupting the resonance to the naphthalene ring.

To establish that the cytotoxic entity was indeed selenium in oxidation state zero, we photobleached MC54 in the presence of an equimolar amount of bovine serum albumin and subjected the resulting Se(0)-albumin conjugates to $^{77}$Se-NMR analysis at the Nuclear Magnetic Resonance (NMR) Laboratories of the University of Wisconsin-Milwaukee. $^{77}$Se—NMR detects organic selenium as well as selenium in oxidation states +II,+IV,+VI, and (in many cases) –II, but not selenium in oxidation state zero. After more than 500 scans with a 500 MHz Bruker NMR spectrometer, we could not detect any selenium resonance. This negative result was thus consistent with the notion that selenium was present in the form of selenium zero. After NMR spectroscopy, one aliquot of the sample was submitted for elemental analysis (performed by Galbraith Laboratories, Knoxville, Tenn.) to verify that the sample contained the expected amount of selenium. A second aliquot of the same was treated with sodium borohydride and benzylchloride ($Ph-CH_2-Cl$) to convert selenium zero into organic selenium. When the latter sample was examined by $^{77}$Se-NMR, a signal indicative of Se in $(Ph-CH_2)_2Se$ was readily detected.

Carrier Proteins: At least three serum macromolecules, albumin, LDL and HDL, were capable of forming cytotoxic conjugates. Only one serum macromolecule, albumin, was capable of forming fluorescent conjugates (Table 2). The role of the (lipo)protein was two-fold, (1) to stabilize the colloidal selenium, and (2) to serve as a delivery vehicle for the cytotoxic entity. In the L1210 leukemia model, conjugates formed by LDL or albumin were more cytotoxic than conjugates formed by HDL. The serum albumin preparations used for these studies were either of bovine or of human origin whereas all lipoprotein fractions were of human origin. When conjugates were formed with human and bovine serum and evaluated for cytotoxic activity against K562 human leukemia cells, the two preparations were equivalent. Both human and bovine serum albumin formed fluorescent conjugates.

TABLE 2

Role of (Lipo)proteins in Formation of Cytotoxic and Fluorescent Conjugates with MC54-Derived Photoproducts

| Solvent/Protein | Fluorescence | Cytotoxic Activity |
| --- | --- | --- |
| Fetal bovine serum | yes | yes |
| Bovine serum albumin | yes | yes |
| Human serum albumin | yes | yes |
| Carboxymethylated bovine serum albumin | yes | no |
| Immunoglubulins (IgG) | no | no |
| Low density lipoprotein (LDL) | no | yes |
| High density lipoprotein (HDL) | no | yes |
| Albumin-depleted fetal bovine serum | no | yes |
| HEPES buffer (10 mM, pH 7.4) | no | no |
| Ethanol | no | no |

Carboxymethylation of albumin prevented the formation of cytotoxic conjugates but did not interfere with the formation of fluorescent conjugates or the binding and uptake of fluorescent conjugates by tumor cells. This suggested that fluorescent and cytotoxic entities interacted with different domains of the albumin molecule. S-Carboxymethyl-albumin was obtained as a commercial product from Sigma Chemical Co. (St. Louis, Mo.). Information provided by the manufacturer indicated that the product contained less than 0.02 mole sulfydryl per mole of albumin and no more than 1.5 moles of S-carboxymethyl-cysteine per mole of albumin.

Figure 7:
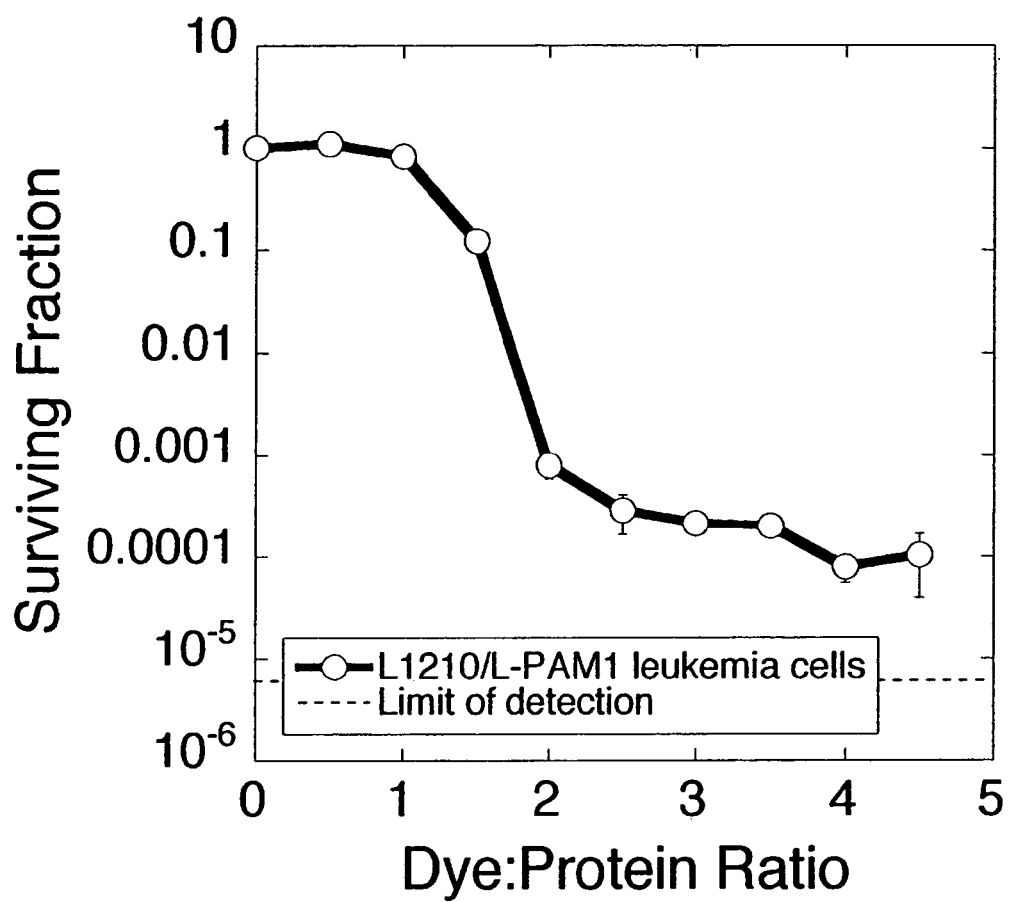
FIG. 7 shows the effect of dye:protein ratios on the cytotoxic activity of Se(0)-protein conjugates. The protein used in the study was bovine serum albumin (Se(0) concentration was kept at 10 μM) and the cell exposure time to the Se(0) conjugates was one hour. The target cells were murine L1210/L-PAM1 leukemia cells. The data points are means of 4 plates±SE (standard error).

Optimal Dye-to-Protein Ratios: For the generation of fluorescent conjugates, the optimal ratio of dye-to-protein is 2:1. For cytotoxic conjugates, the optimal dye-to-protein ratio appears to be about 5:1 (FIG. 7). The fluorescence yield of fluorescent photoproduct-albumin conjugates was determined with a Hitachi F4500 fluorescence spectrophotometer. All samples were serially diluted with buffer to rule out artifacts due to self-quenching. In vitro clonal assays of L1210 murine leukemia cells were used to assess cytotoxic activity.

Figure 6:
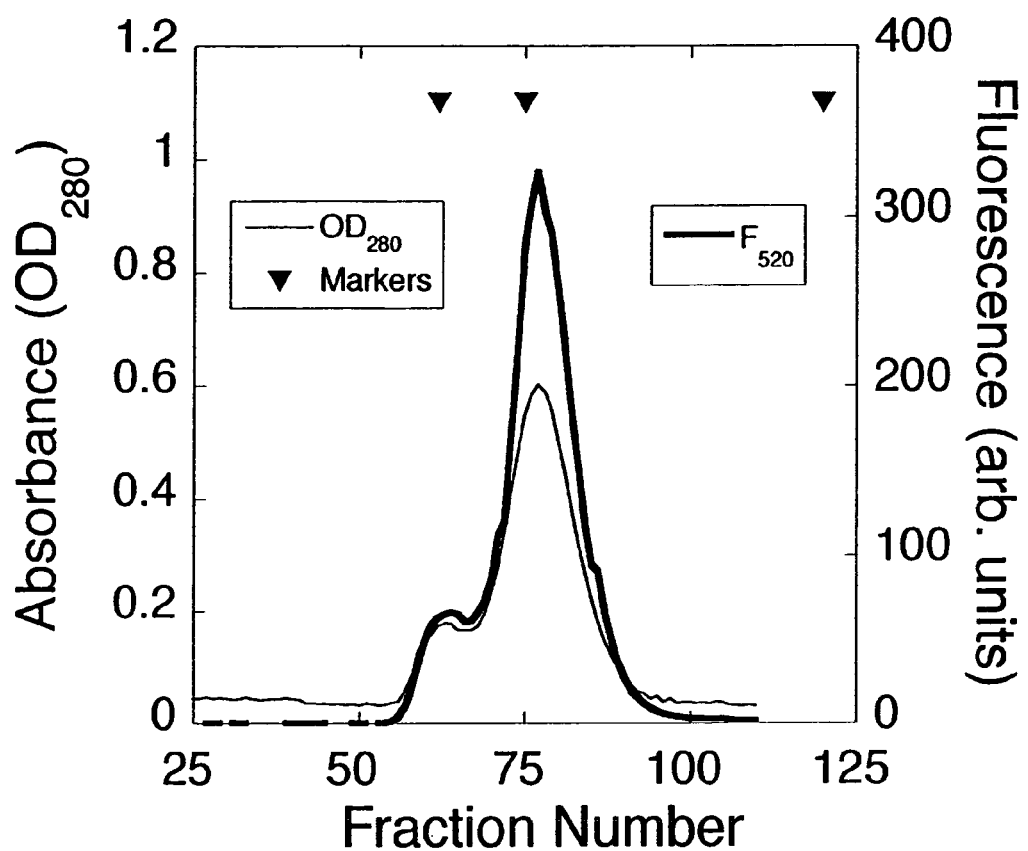
FIG. 6 shows the result of a gel filtration chromatography of fluorescent photoproduct-protein conjugates on Sephadex G-100. The triangles indicate the elution peaks of three marker proteins, bovine serum albumin dimer (left), bovine serum albumin monomer (middle), and carbonic anhydrase (right).

Bond between Photoproducts and Carrier Proteins: We initially favored the view that photoproducts formed covalent bonds with carrier proteins because fluorescent/cytotoxic conjugates were resistant to extraction with organic solvents, detergents, high concentrations of salt, and chaotropic agents. Both the cytotoxic and the fluorescent entity were co-precipitated with albumin by the addition of 4 volumes of cold ethanol or acetone. Furthermore, the fluorescent entity co-eluted with albumin monomers and dimers when chromatographed on Sephadex G-100 (FIG. 6). However, recent experiments indicate that the green-fluorescent moiety can be displaced from the protein by a 10-fold molar excess of 8-anilino-1-naphthalene-sulfonic acid (ANS). One explanation for this remarkably strong yet probably non-covalent bond between chromophore and albumin is that the amphipathic chromophore photoproduct forms both lipophilic and ionic bonds with albumin. Organic solvents, detergents, and concentrated salt solutions break only one type of bond and leave the other bond intact. ANS, on the other hand, is an amphipathic molecule and may therefore be better able to displace the chromophore photoproduct from albumin. However, at this stage, the exact nature of the bond(s) between the photoproducts and carrier proteins is not totally clear.

EXAMPLE 2

Chemical Methods for Preparation of Colloidal Selenium and Se(0)-Protein Comjugates Preparation of Colloidal Selenium by Chemical Reduction of Selenium dioxide: We have tried two well-established methods for the preparation of colloidal selenium based on the reduction of selenium dioxide by sodium borohydride or ascorbic acid in the presence of bovine serum albumin (See Table 3). Both preparations have been found to be cytotoxic.

TABLE 3

(1) $SeO_2 \xrightarrow{\text{Reducing agent*}} Se(0)$ colloidal
*) e.g. $NaBH_4, N_2H_4, SO_2, HI, CNBH_2$ (2) $SeO_2 + 2 C_6H_6O_6 \longrightarrow Se(0)$ colloidal $+ 2 C_6H_6O_6$
(ascorbic acid)

To counter the argument that the cytotoxic activity of our Se(0)-protein conjugates was attributable to contaminating selenium dioxide, we exposed control cells to equimolar (up to 30 µM) concentrations of selenium dioxide instead of Se(0)-protein conjugates. Selenium dioxide was not cytotoxic at of the tested concentrations while Se(0)-protein conjugates eliminated $\geq 4$ log of L1210 leukemia cells.

Preparation of Colloidal Selenium by Chemical Reduction of Selenious Acid: The method provided here involves a reaction that can be made to run forwards and backwards simply via adjustment of the pH. The first reaction involves elemental selenium and elemental iodine in the presence of sodium bicarbonate (or any other suitable pH 7 buffer) that dissolves both components: $Se + 2I_2 + 6NaHCO_3 \rightarrow Na_2SeO_3 + 4NaI + 6CO_2 + 3H_2O$ The colorless reaction mixture can then be diluted and optionally mixed with the carrier protein. When that mix is acidified, the reaction runs in the opposite direction, producing elemental selenium in finely divided form and elemental iodine: $H_2SeO_3 + 4HI \rightarrow Se + 2I_2 + 3H_2O$ Such acidification may be by addition of a soluble acid to pH 3–4, but may also advantageously involve an insoluble acid, such as Dowex 50 ion exchange resin in $H^+$ form. The iodine can effectively be removed by entrapment into insoluble starch particles (mixing or column filtration, even by starch sizing on paper) after which the pH should be adjusted back to a working level that is biologically tolerated. An alternate implementation would be to provide an aqueous solution of $SeO_2$, add a stoichiometric quantity of sodium or potassium iodide, then dilute as desired, and treat with the acid source and the iodine removal process.

An advantage of the method provided here is that the reactions can be run under conditions well tolerated by proteins and adjuvants in aqueous solution. In addition, both reaction components are present in the exact required stoichiometry. Further, the particle sizes of the resulting selenium and the reaction rate of this 2nd order reaction can be varied over a wide range simply by manipulating the dilution. An additional benefit of such a reaction is sterilization by virtue of having all material and vessels exposed to an effective antiseptic dose of iodine.

EXAMPLE 3

Binding, Uptake, Subcellular Localization, and Cytotoxic Mechanisms of Photoproduct-Protein Conjugates Materials and Methods Binding and internalization of selenomerocyanine-derived Se(0)-protein conjugates by cells: Fluorescent conjugates were prepared by photobleaching selenomerocyanine dye in the presence of fetal bovine serum as described in Example 1. Cells were subsequently incubated with fluorescent conjugates (13 µM) for graded periods of time, and binding/uptake was measured with a flow cytometer (FACStar, Becton Dickinson, Mountainview, Calif.) equipped with 15 mW argon ion laser (480 nm line) using standard fluorescein filter settings (525/30 nm bandpass filter). Data were processed using the CellQuest (Bescton Dickinson) software package.

Temperature-dependence of conjugate uptake and conjugate-mediated cell killing: Selenomerocyanine dye MC54 was added from a 67× stock solution (in ethanol) to alpha-medium supplemented with 12% fetal bovine serum to achieve a final dye concentration of 26 µM. The mixture was exposed to white light (fluence rate: 27 $W/m^2$) for 60 min and subsequently used for conjugate binding/uptake and cytotoxicity experiments. L1210 leukemia cells ($10^6$/ml) were incubated with the conjugate solution at 0° C. or 37° C. for graded time intervals. Conjugate uptake was determined by flow cytometry as described above. The survival of in vitro clonogenic cells was determined by clonal assay as described above.

Level of intracellular thiols of L1210/L-PAM1 leukemia cells by 1-hour exposure to cytotoxic Se(0)-protein conjugates: Cytotoxic conjugates were prepared by photobleaching selenomerocyanine dye MC54 for 60 min in alpha-medium supplemented with 12% fetal bovine serum. Cells ($10^6$/ml) were incubated with conjugates at 37° C. for 1 hour, washed, and probed for glutathione with the fluorescent thiol probe, monochlorobimane (Molecular Probes, Eugene, Oreg.) as described by Hedley and Chow (D W Hedley, S Chow: Evaluation of methods for measuring cellular glutathione content using flow cytometry. Cytometry 15: 349–358 (1994)).

Results and Discussions

Figure 8A:
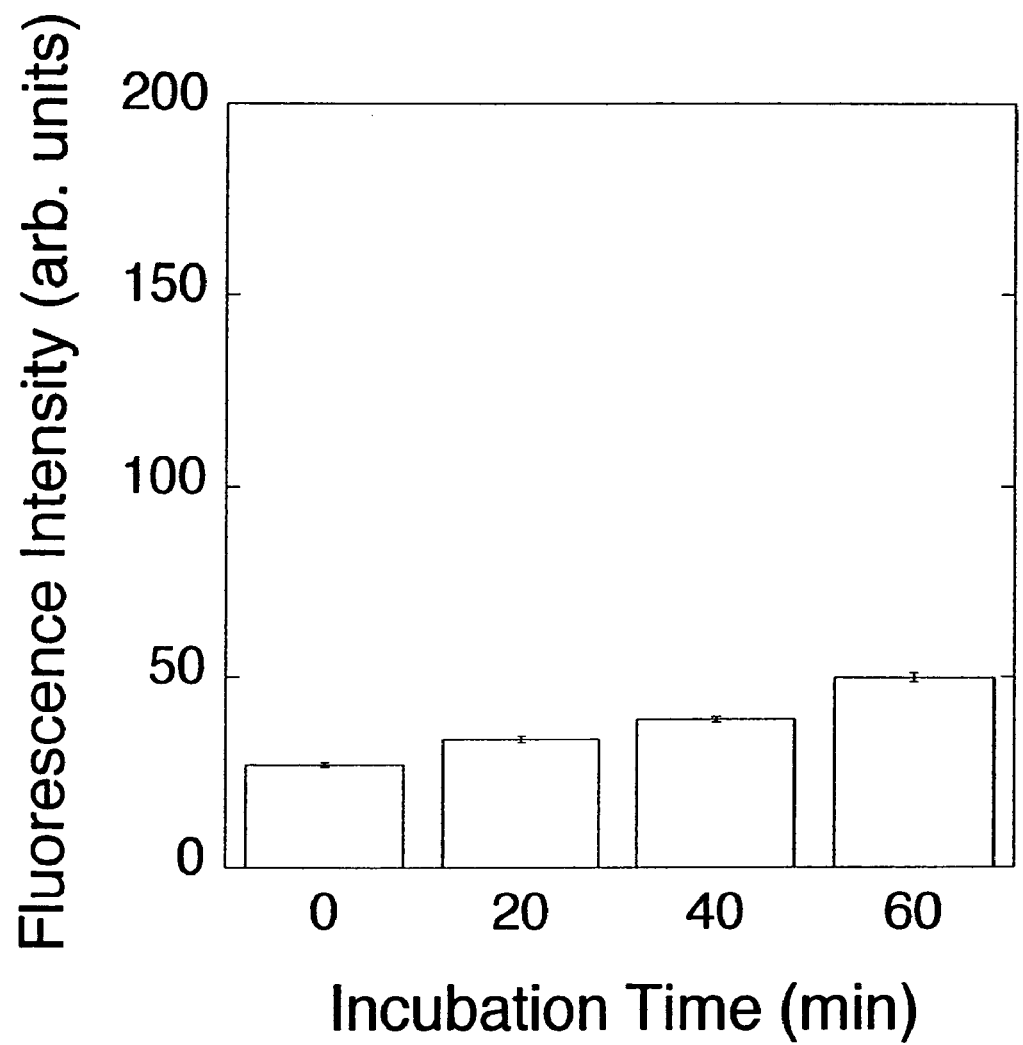
FIG. 8 shows binding/uptake of fluorescent photoproduct-albumin conjugates by L1210 murine leukemia cells (a), DU-145 human prostate cancer cells (b) and MDA-MB-435 human breast cancer cells (c). The data points represent mean colony counts of 4 culture plates±SE.
Figure 8B:
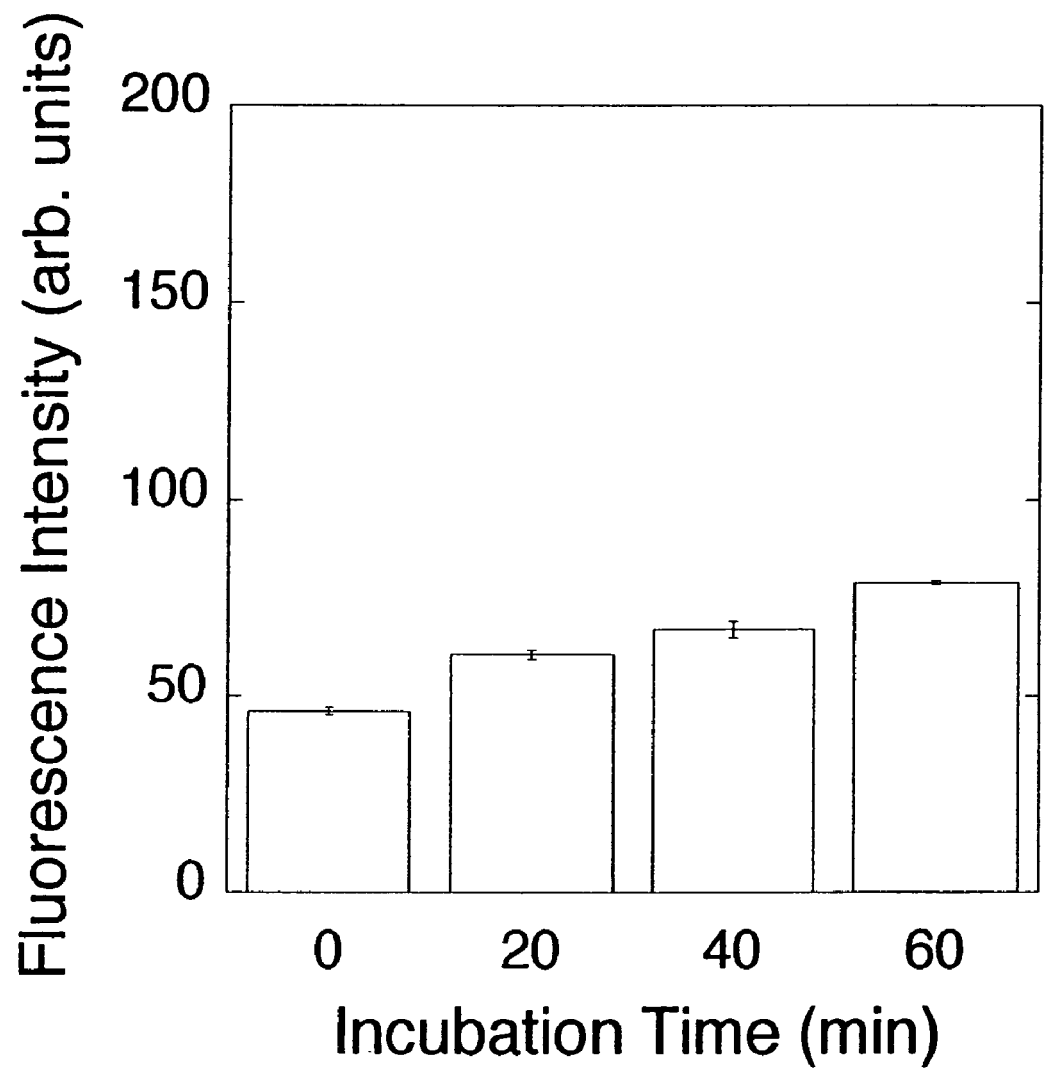
Figure 8C:
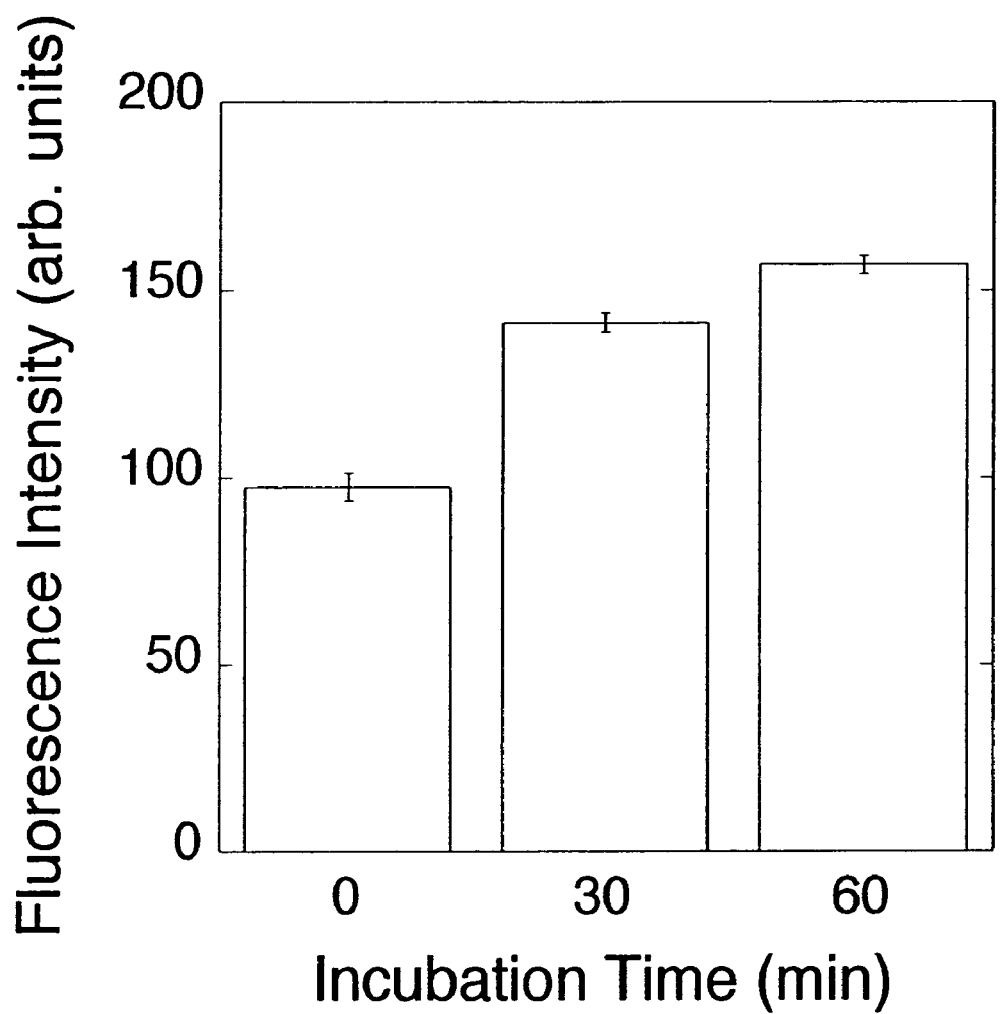

Binding and internalization of selenomerocyanine-derived Se(0)-protein conjugates by cells: When tested with the murine leukemia cell line L1210, the human prostate cancer cell line DU-145, and the human breast cancer cell line MDA-MB-435, selenomerocyanine-derived Se(0)-protein conjugates were bound and internalized by these cells (FIG. 8: a, L1210 leukemia cells; b, DU-145 prostate cancer cells; c, MDA-MB-435 breast cancer cells). The higher fluorescence values determined for breast and prostate cancer cells in part reflect the larger average size of these cells.

Figure 9A:
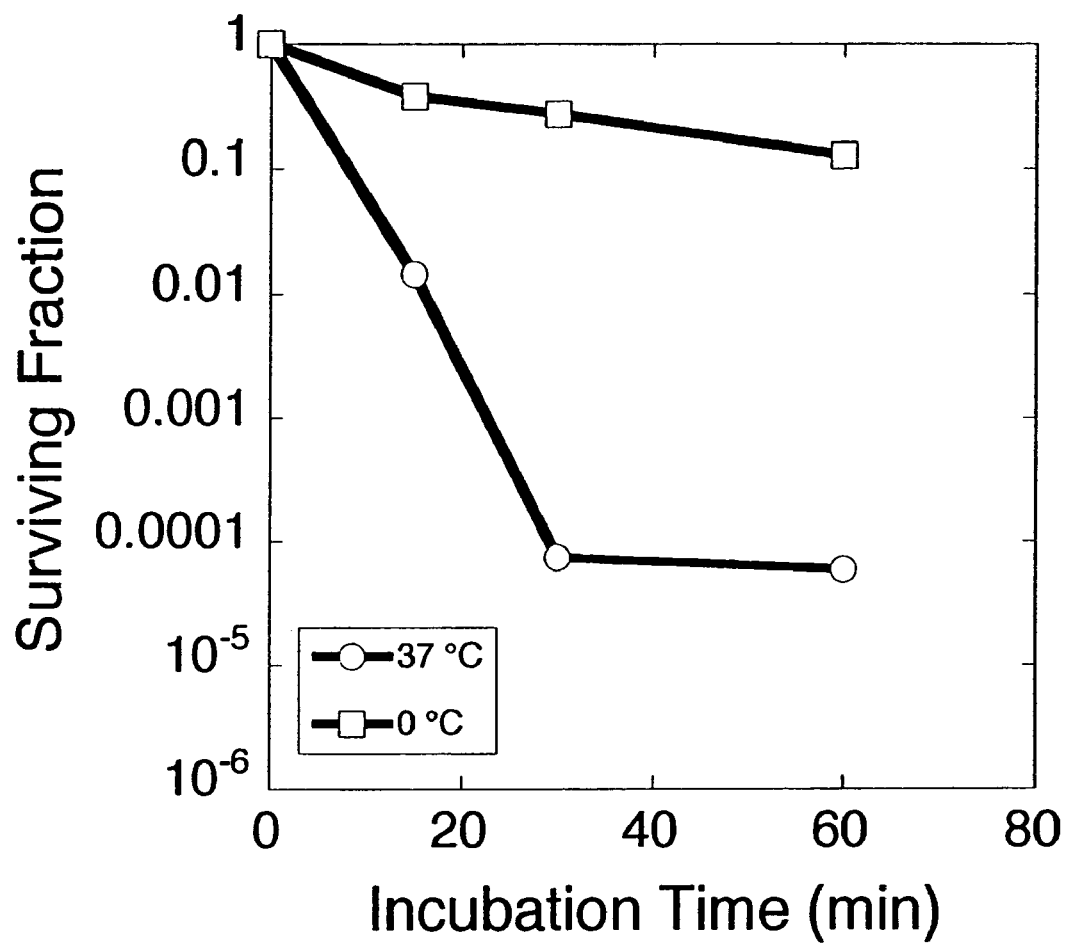
FIG. 9 shows that killing of L1210 leukemia cells by Se(0)-protein conjugates (a) and uptake of fluorescent selenomerocyanine-derived photoproduct-protein conjugates (b) are temperature dependent. The protein source used for the study was fetal bovine serum (Se(0) concentration was 26 µM) and the cells were L1210 leukemia cells.
Figure 9B:
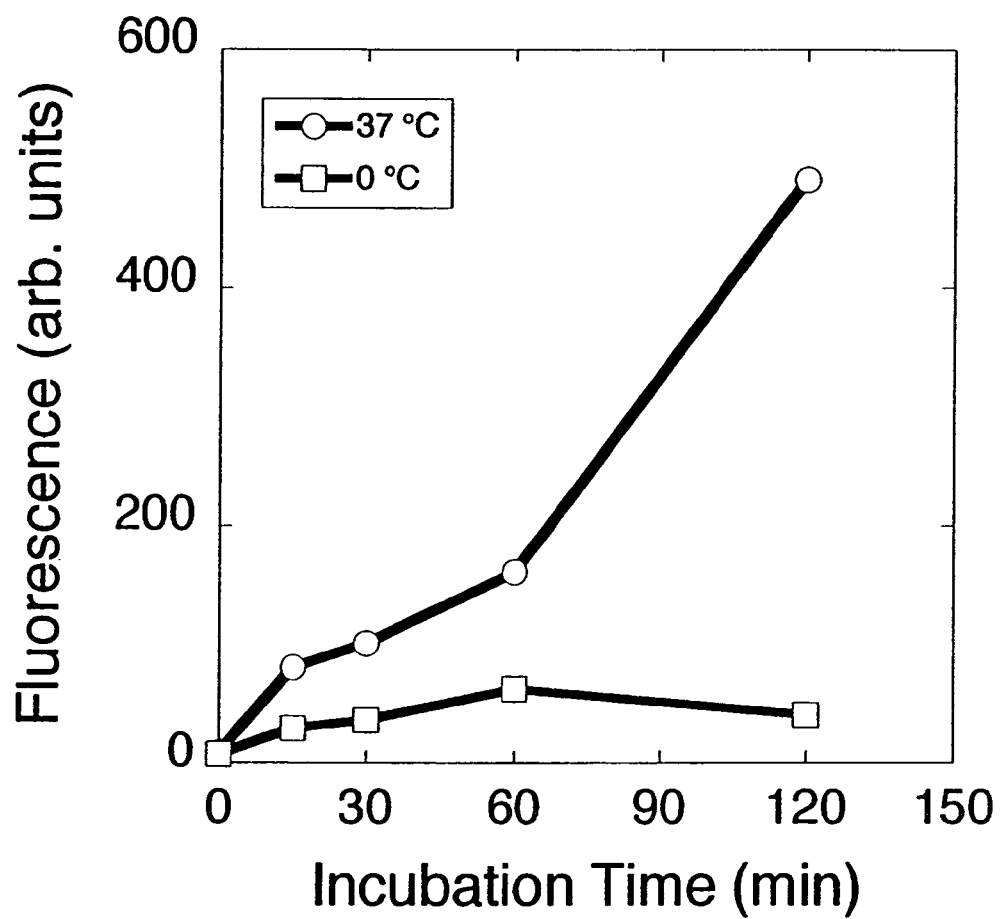

Temperature-dependence of conjugate uptake and conjugate-mediated cell killing: Low temperatures inhibited the uptake of fluorescent conjugates and protected cells against the cytotoxic activity of conjugates (FIGS. 9a and 9b). This behavior is consistent with an energy-dependent endocytotic process. This behavior is also consistent with the notion that Se(0)-protein conjugates are not cytotoxic unless they are internalized by target cells. Conjugate uptake and cytotoxic activity were also a function of incubation time (FIGS. 9a and 9b).

Binding/Uptake and Subcellular Localization of Photoproduct-Protein Conjugates: The uptake and cytotoxic action of fluorescent/cytotoxic photoproduct-albumin conjugates by tumor cells was inhibited by cytochalasin B and by low temperature (5° C.), suggesting that conjugates were internalized by an energy-dependent endocytotic process. When sparse cultures of Mm5MT breast cancer were incubated with MC54-derived green-fluorescent photoproduct-albumin conjugates and with LysoTracker Red (a red-fluorescent probe for lysosomes; Molecular Probes) many lysosomes in merged images were yellow-fluorescent, indicating that LysoTracker Red and fluorescent conjugates were co-localized in the same organelle.

Role of Intracellular and Extracellular Glutathione: Early pilot experiments had shown that melphalan-resistant mutant L1210 leukemia cells that were characterized by an elevated content of intracellular glutathione (GSH) were more sensitive to Se(0)-protein conjugates than the corresponding wild-type cells. This prompted speculations about a potential role of intracellular GSH in the bioactivation of internalized cytotoxic conjugates. Subsequent experiments, however, showed that mutant L1210 cells were more sensitive to conjugates because they internalized cytotoxic conjugates at a higher rate than wild-type cells. Inhibition of GSH biosynthesis made cells more sensitive to cytotoxic conjugates.

Co-incubation with reduced (GSH) or oxidized (GSSG) glutathione (1 mM) reduced the cytotoxic effect of Se(0)-protein conjugates by about 50%. Co-incubation with GSH did cause a modest increase in intracellular glutathione levels. However, the increase appeared too small to fully explain the strong protective effect of extracellular GSH. Extracellular GSH did not inhibit the uptake of fluorescent conjugates. To the contrary, in most experiments, it slightly enhanced the uptake of conjugates. However, we do not yet know if the fluorescent conjugates whose uptake was measured still contained the cytotoxic entity. To determine if GSH facilitated the dissociation of Se(0) from Se(0)-albumin conjugates, conjugates were dialyzed against a buffer that contained GSH (1 mM) and albumin. When equilibrium was reached, the selenium content inside and outside the dialysis bag was determined by quantitative elemental analysis (performed by Galbraith Laboratories). All selenium was recovered inside the dialysis bag, suggesting that GSH either did not dissociate Se(0) from the carrier protein or that displaced colloidal selenium particles were unable to cross the 5,000 Dalton pores of the dialysis membrane. Pretreating cells with GSH or GSSG was not protective.

Figure 10:
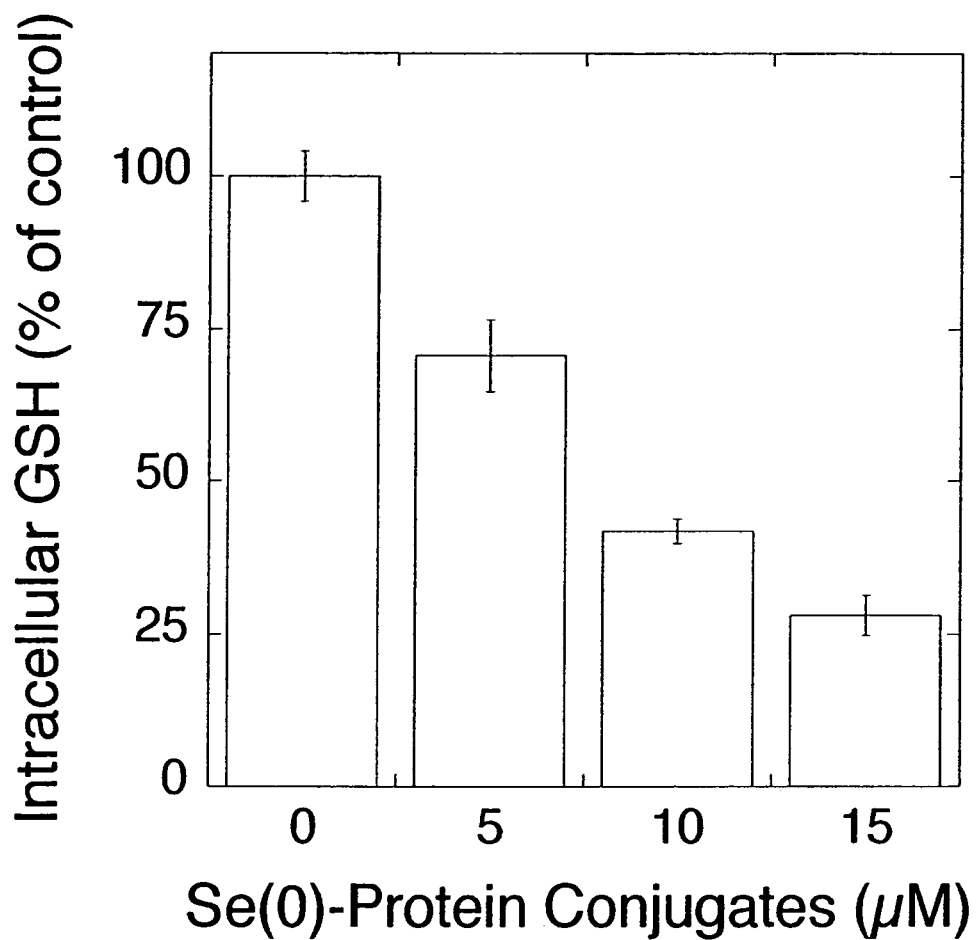
FIG. 10 shows that incubating L1210/L-PAM1 leukemia cells with Se(0)-protein conjugates for one hour reduces intracellular thiols in the cells. The exposure time was one hour. The data points are means of 4 determinations±SE.
Figure 11:
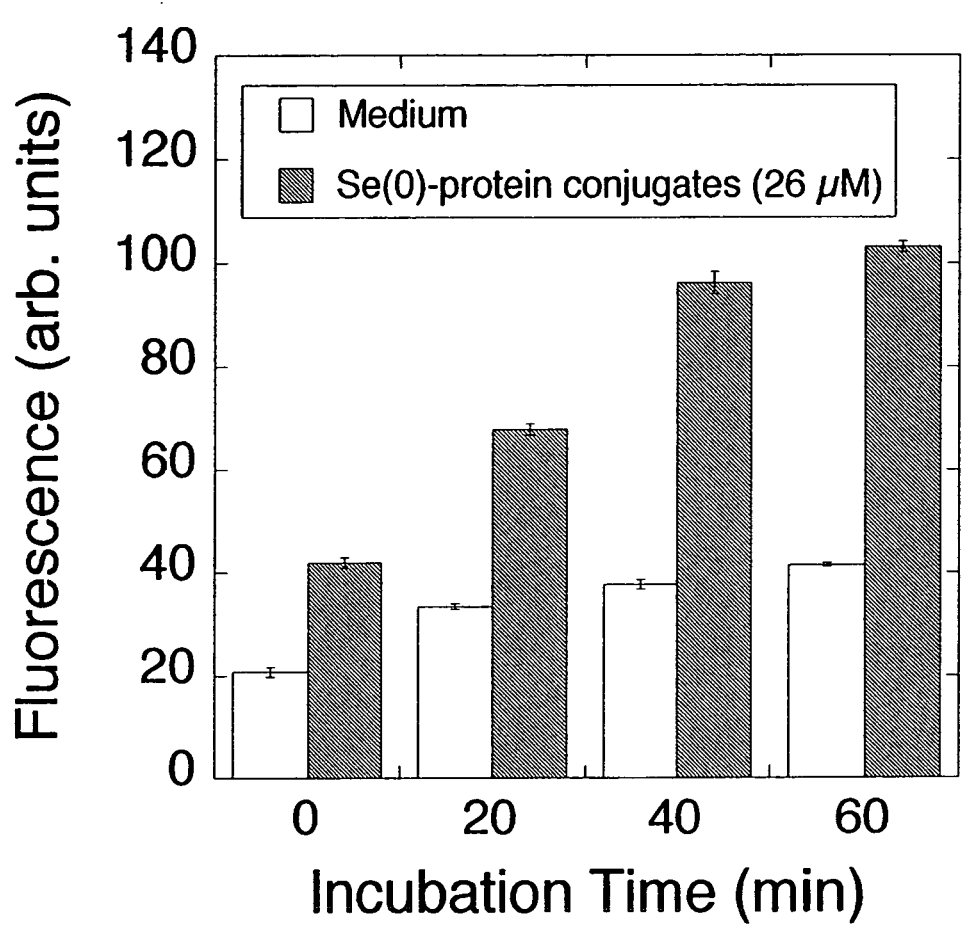
FIG. 11 shows oxidation of DCFH by Se(0)-protein conjugates. The protein source was fetal bovine serum. The conjugate concentration was 26 µM. The data points are means of 4 determinations±SE.

Rapid Depletion of Intracellular Glutathione by Internalized Se(0)-Protein Conjugates: In highly sensitive L1210 or L1210/L-PAM1 leukemia cells, the uptake of Se(0)-protein conjugates caused a rapid depletion of intracellular GSH (FIG. 10). Glutathione levels in the supernatant of treated cells were also reduced suggesting that the loss of intracellular GSH was not the result of leakage but the result of an oxidative event. 2',7'-dichlorodihydrofluorescein diacetate ($H_2DCFDA$) is a useful (albeit not very specific) probe for assessing oxidative stress in cells (Oyama, Y. et al., 1994; Trayner, I. D. et al., 1995). Leukemia cells that had been exposed to Se(0)-protein conjugates showed higher levels of $H_2DCF$ than untreated control cells, indicating oxidative stress. The oxidation of $H_2DCF$ by Se(0)-protein conjugates could also be demonstrated in a cell-free system that contained only DCFH (generated by mild alkaline hydrolysis of $H_2DCFDA$), Se(0)-protein conjugates, and HEPES-buffer (FIG. 11). Taken together, these data strongly suggest that Se(0)-protein conjugates act as air oxidation catalysts that catalyze the rapid oxidation of thiols.

Spallholz and coworkers have presented evidence that covalent adducts of proteins and selenium compounds (containing Se in oxidation states other than zero) generate hydrogen peroxide and superoxide anion (Lin, Y. et al., 1993; Stewart, M. S. et al., 1997; Davis, R. L. et al., 1998). To assess the role of hydrogen peroxide and superoxide anion in the cytotoxic action of Se(0)-protein conjugates, we exposed L1210 leukemia to cytotoxic doses of conjugates and subsequently probed the cells using the luminol- and luminogenin-based tests described by Spallholz and colleagues (Lin, Y. et al., 1993; Stewart, M. S. et al., 1997; Davis, R. L. et al., 1998). The results of both tests were negative, suggesting that peroxide and superoxide anion were not important cytotoxic mediators of our Se(0)-protein conjugates.

Role of Apoptosis in the Cytotoxic Pathway of Se(0)-Protein Conjugates: When HL-60 leukemia cells were exposed to Se(0)-protein conjugates (26 µM) for 30 min, the concentration of annexin V-positive cells increased from 3.5% to 31%. Average cell volumes (as determined by forward light scatter) decreased as a function of conjugate exposure. An electron microscopic analysis of conjugate-treated HL-60 leukemia cells showed evidence of nuclear fragmentation, apoptotic bodies, and swollen mitochondria.

Figure 12:
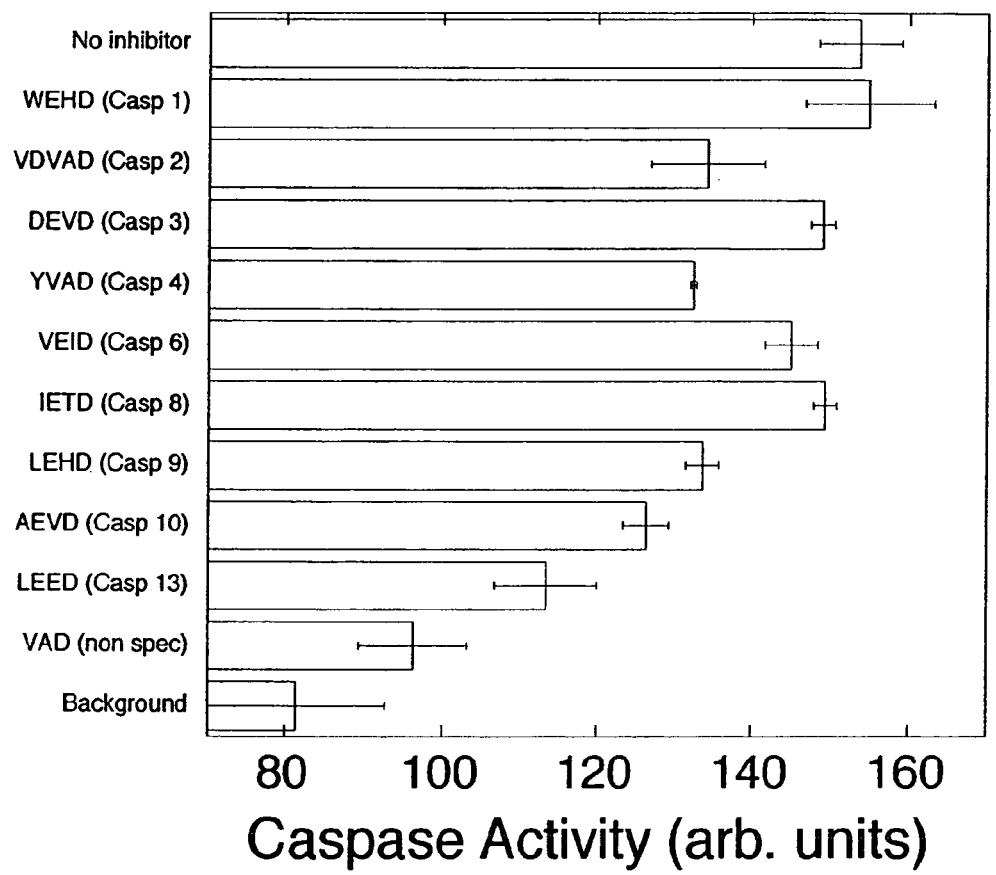
FIG. 12 shows activation of caspase activity in L1210 leukemia cells after exposing the cells to Se(0)-protein conjugates (26 µM) for 30 minutes. Conjugates were derived from MC56 to avoid a spectral interference with the fluorescent caspase substrate. The protein source was fetal bovine serum. Caspase inhibitors were used as recommended by the manufacturer (R&D Systems). That is, each sample contained $10^6$ cells, and the final concentration of inhibitors was 0.1 mM. Incubation was at 37° C. for 1 hour. The "Z"-prefix of the inhibitor names indicates that the inhibitors were synthesized with a benzyloxycarbonyl group to enhance cellular peremability.

We have used the Oncogene (San Diego, Calif.) Caspase Detection Kit to monitor caspase activity in L1210 leukemia cells after exposure to cytotoxic Se(0)-protein conjugates. The kit uses a fluorescent substrate (FITC-VAD-FMK; a conjugate of fluoresceinisothiocyanate with a fluoromethylketone-derivaticed short peptide) that detects a broad range of caspases. When FITC-VAD-FMK is used in conjunction with non-cytotoxic concentrations of specific peptide inhibitors (R&D Systems, Minneapolis, Minn.), the inhibition of the fluorescent signal is directly proportional to the contribution of the respective caspases to the overall signal. As FIG. 12 shows, among the specific inhibitors, Z-LEED-FMK (inhibitor of caspase 13) was most effective followed in order of decreasing potency by specific inhibitors of caspases 10, 4, 9, 2, 6, 3, 8, and 1. As expected, the non-specific caspase inhibitor, Z-VAD-FMK, which inhibits a broad range of caspases, reduced the fluorescence signal more than any of the specific inhibitors. Taken together, these data indicate that in L1210 leukemia cells, cytotoxic Se(0)-protein conjugates activate primarily caspases 10 and 13. Caspases 2, 4 and 9 show moderate activation whereas caspases 1, 3, 6 and 8 show little or no activity. The low level of caspase 8 activity is consistent with a cytotoxic mechanism that does not involve cell surface death receptors. It is conceivable that somewhat different activity profiles will be obtained when investigations are extended to other cell types or when caspase activity is tested at different time intervals after exposure to cytotoxic conjugates.

Molecular Basis of Selective Cytotoxicity: In leukemia and lymphoma cells (which happened to be of similar size), sensitivity to Se(0)-protein conjugates correlated primarily with the uptake of conjugates and secondarily with intracellular GSH levels. When investigations were extended to solid tumor cells, the situation became more complex, with some cell lines showing only moderate sensitivity to Se(0)-protein conjugates despite extensive uptake of conjugates. A preliminary analysis of the data suggests that in addition to conjugate uptake and GSH content, there may be a third determinant of sensitivity to Se(0)-protein conjugates.

EXAMPLE 4

Role of Cytotoxic Photoproduct-Protein Conjugates in Merocyanine-PDT

Materials and Methods

Cytotoxic activity of Cytotoxic Se(0)-protein conjugates: Selenomerocyanine dye MC54 was added from a 67× concentrated stock solution in ethanol to a final concentration of 26 µM in alpha-modified Dulbecco's medium (alpha-medium) supplemented with 10% fetal bovine serum or 10% human serum, respectively and exposed to cool white fluorescent light (fluence rate: 27 W/m$^2$) for 60 min to generate cytotoxic Se(0)-protein conjugates. Cytotoxic conjugate-containing medium was mixed with alpha-medium in various ratios to achieve Se(0)-protein concentrations of 0–26 µM. Cells (10$^6$/ml) were incubated in these mixtures at 37° C. for 60 min. The surviving fraction of in vitro clonogenic cells was determined by in vitro clonal assay as described in Sieber, F. et al., 1987, which is incorporated by reference in its entirety.

Results

Figure 13:
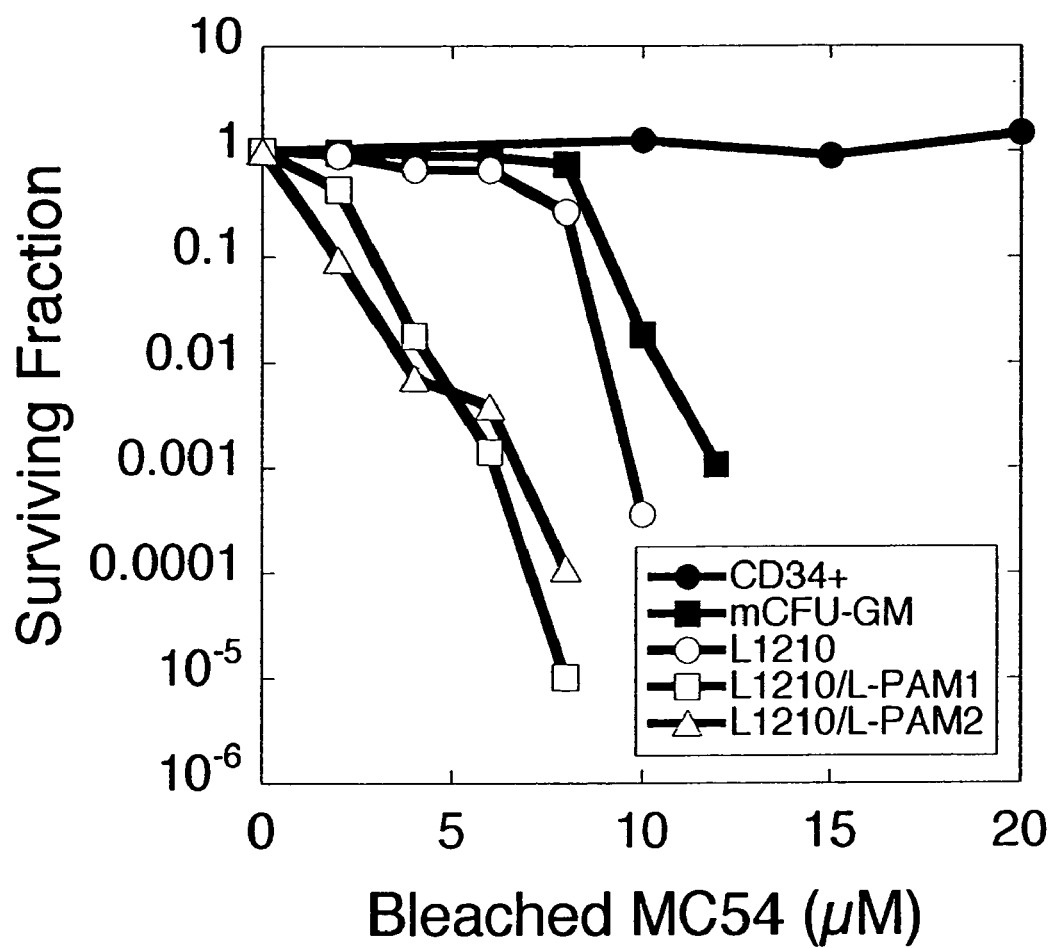
FIG. 13 shows differential sensitivity of murine normal (CD34-positive stem cells and granulocyte/macrophage progenitors (mCFU-GM)) and neoplastic (wild-type L1210 leukemia cells and melphalan-resistant mutant L1210/L-PAM1 and L1210/L-PAM2 leukemia cells) hematopoietic cells to Se(0)-protein conjugates (after one hour exposure). The protein source was fetal bovine serum. The survival of of mCFU-GM, L1210, L1210/L-PAM 1, and L1210/L-PAM2 cells was determine by in vitro clonal assay. The yield of CD34-positive cells was determined flow cytometrically after staining with a FITC-conjugated anti-CD34 antibody. The data points are means of 4 plates or determinations±SE.
Figure 14:
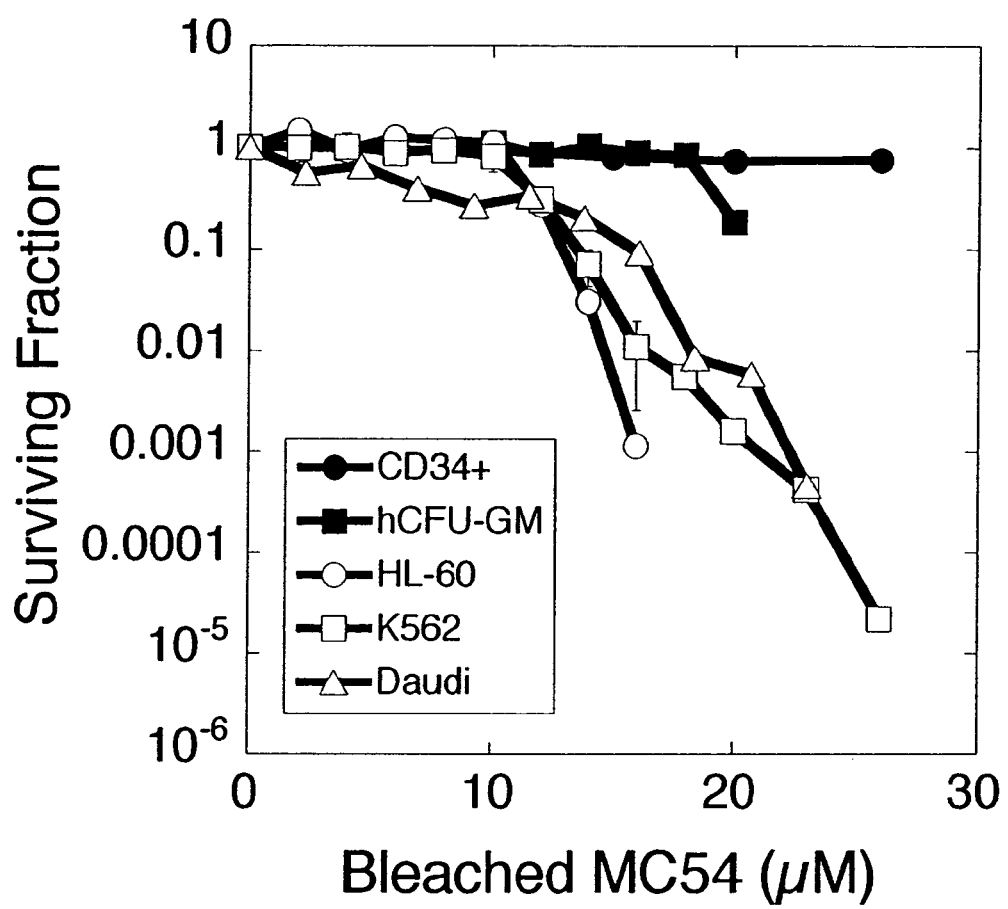
FIG. 14 shows differential sensitivity of human normal (CD34-positive stem cells and granulocyte/macrophage progenitors (hCFU-GM) and neoplastic (HL-60 and K562 leukemia cells and Daudi lymphoma cells) hematopoietic cells to Se(0)-protein conjugates (after one hour exposure). The protein source was fetal bovine serum. The yield of CD34-positive cells was determine flowcytometrically after staining with a FITC-conjugated anti-CD34 antibody. The survival of hCFU-GM andf HL-60, K562, and Daudi cells was determined by in vitro clonal assay. The data points are means of 4 plates or determinations±SE.

Spectrum of Antineoplastic Activity: We have tested Se(0)-protein conjugates on the panel of tumor cell lines shown in Table 4. All leukemia and lymphoma cell lines were highly sensitive to Se(0)-protein conjugates (FIGS. 13 and 14). Tumor cell depletions of ≧5 log could be obtained with little or no damage to normal hematopoietic stem (CD34-positive) and progenitor (CFU-GM) cells. The response of solid tumor cells was variable, even within a single tumor cell type. For example, if one set of conditions (26 µM conjugates; 60 min) reduced MDA-MB-231 breast cancer cells 9,346-fold, the same set of conditions reduced BT-20 breast cancer cells just 7-fold.

TABLE 4

| Leukemia and Lymphoma: | L1210[a] L1210/L-PAM1[a] L1210/L-PAM2[a] | P388[a] P388/ADR[a] Daudi[b] | HL-60[b] HL-60/ADR[b] K562[b] |
|---|---|---|---|
| Breast Cancer: | C1271[a] Mm5MT[a] MM 060562[a] T-47D[b] | MDA-MB-435[b] MDA-MB-231[b] SK-BR-3[b] | MCF7[b] BT-20[b] MDA-MB-468[b] |
| Neuroblastoma: | Neuro 2a[a] | SK-N-SH[b] | |
| Ewing's Sarcoma | SK-ES-1[b] | | |
| Medulloblastoma: | D283[b] | | |
| Lung Cancer: | H69[b] H69/CDDP[b] | PC14[b] PC14/CDDP[b] | |
| Ovarian Carcinoma: | OVCAR-3[b] | | |

[a]murine;
[b]human

The fact that most solid tumor cells were only reduced 100- to 1,000-fold by a 1-hour incubation with Se(0)-protein conjugates (26 µM) does not argue against the use of Se(0)-protein conjugates in solid tumors. All solid tumors responded to dose escalation, and doses in excess of 26 µM may be feasible since CD34-positive hematopoietic stem cells may well tolerate conjugate concentrations in excess of 26 µM. Furthermore, pilot experiments with DU145 prostate cancer cells indicate that longer incubation times (up to 6 hours) significantly enhance tumor cell kill.

Sensitivity of Drug-Resistant Mutant Tumor Cells to Cytotoxic Se(0)-Protein Conjugates: Our survey of tumor cell lines included several sets of drug-resistant and wild-type cells. Melphalan-resistant L1210/L-PAM1 and L1210/L-PAM2 cells (characterized by elevated levels of intracellular glutathione (Ahmad, H. et al., 1987)) were more sensitive to Se(0)-protein conjugates than the corresponding wild-type L1210 cells (FIG. 14). The increased sensitivity was related to enhanced conjugate uptake rather than to increased GSH levels. Cis-platin-resistant PC14/CDDP lung cancer cells (reduced uptake of drug (Ohmori, T. et al., 1993)) were slightly less sensitive to conjugates than wild-type PC14 cells. The reduced sensitivity correlated with reduced conjugate uptake. Cis-platin-resistant H69/CDDP lung cancer cells (characterized by elevated levels of GSH, metallothionein, and glutathione-S-transferase-pi (Kasahara, K. et al., 1991)) and adriamycin-resistant P388/ADR (overexpression of P-glycoprotein) leukemia cells were as sensitive as their wild-type counterparts. Adriamycin-resistant HL-60/ADR leukemia cells (MRP-mediated drug efflux (Krishnamachary, N. et al., 1993)) were slightly less sensitive to conjugates than wild-type HL-60 cells. The reduced sensitivity correlated with reduced conjugate uptake. Depriving HL-60/ADR cells of glucose (to inhibit the MRP-mediated drug export) restored the uptake of conjugates to near-normal levels. Taken together, these data suggest that therapy with Se(0)-protein conjugates is only minimally affected by common drug resistance mechanisms.

Toxicity to Primitive Hematopoietic Stem Cells: Studies on the toxicity of Se(0)-protein conjugates to normal hematopoietic stem and progenitor cells have been extended to murine and human CD34-positivecells. To avoid spectral interference between FITC-labeled anti-CD34 antibodies and photoproduct-albumin conjugates, cytotoxic conjugates were prepared by photobleaching MC56 rather than MC54 (conjugates formed by MC56 are non-fluorescent but as cytotoxic as those formed by MC54). As FIGS. 13 and 14 indicate, both human and murine CD34-positive stem cells were resistant to cytotoxic Se(0)-protein conjugates.

Figure 15:
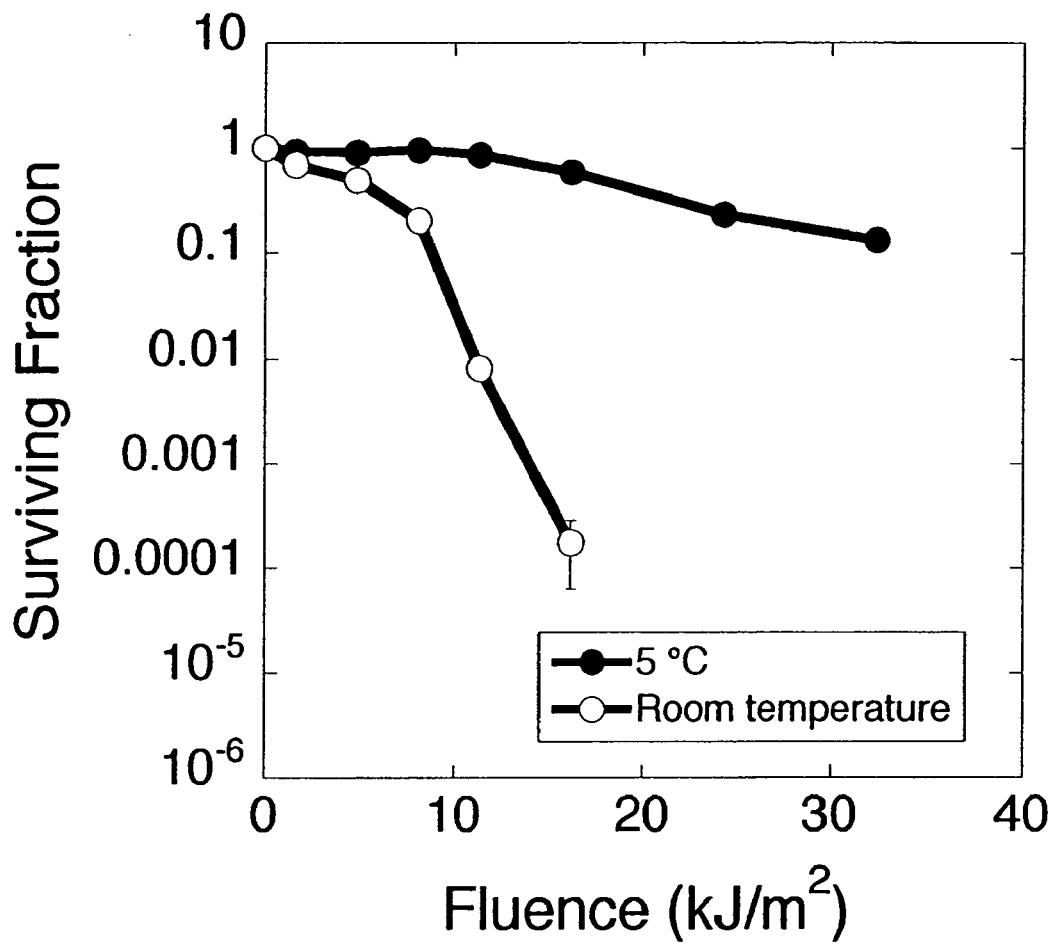
FIG. 15 shows the effect of temperature on the MC54-sensitized photoinactivation of L1210 leukemia cells. The dye concentration was 13 µM. The data points are means of 4 plates±SE.

Role of Se(0)-Protein Conjugates in Photodynamic Therapy: FIG. 15 illustrates that under certain experimental conditions, cytotoxic Se(0)-protein conjugates can play a dominant role in selenomerocyanine-mediated photodynamic therapy (PDT). The survival curve recorded at room temperature shows the combined cytotoxic effect of MC54-PDT and MC54-derived photoproduct-protein conjugates. The survival curve recorded at 5° C. shows only the effect of MC54-PDT only. The large difference between the two curves reflects the contribution of MC540-derived cytotoxic conjugates. Depending on the tumor cell of interest, conditions favoring the uptake of Se(0)-protein conjugates may thus enhance or reduce the therapeutic index of PDT. When the targets are L1210/L-PAM1 or L1210/L-PAM2 cells, it would obviously be of advantage to choose experimental conditions that favor conjugate uptake as these cells are quite resistant to PDT (i.e. singlet oxygen-mediated damage to plasma membrane) but exceptionally sensitive to Se(0)-protein conjugates.

EXAMPLE 5

Comparison of the Cytotoxic Activities of Se(0)-Protein Conjugates and 4-Hydroperoxycyclophosphamide (4-HC)

Methods

Cytotoxic Se(0)-protein conjugates were generated by exposing alpha-medium supplemented with fetal bovine serum (10%) and selenomerocyanine photosensitizer MC54 (26 µM) to cool white fluorescent light (fluence rate: 27 W/m$^2$) for 60 min. Wild-type L1210 leukemia cells, melphalan-resistant mutant L1210/L-PAM1 cells, or normal murine granulocyte/macrophage progenitors (mCFU-GM) ($10^6$/ml) were suspended either in cytotoxic conjugates or in alpha-medium supplemented with 4-HC (10 µg/ml) and incubated for 45 min at 37° C. Treatment conditions were selected to achieve a similar recovery of normal murine hematopoietic progenitor cells (mCFU-GM). Cells were washed free of excess conjugates or drug, and surviving fractions were determined by in vitro clonal assay.

Results

The results are shown in Table 5. Cytotoxic conjugates were more potent and more selective than 4-HC in killing the tumor cells. 4-HC killed more normal cells than tumor cells while conjugates killed more tumor cells than normal cells.

TABLE 5

| | Surviving Fraction | |
|---|---|---|
| Cell Type | Conjugates (26 µM, 45 min) | 4-HC (10 µg/ml, 45 min) |
| mCFU-GM | 0.0096 ± 0.0013 | 0.0088 ± 0.0025 |
| L1210 | <0.000003* | 0.0460 ± 0.0043 |
| L1210/L-PAM1 | <0.000003* | 0.2636 ± 0.0074 |

*Limit of detection.

EXAMPLE 6

Evaluation of Photoproduct-Protein Conjugates for Systemic Therapy

Materials and Methods

Effect of native albumin on cytotoxicity of Se(0)-albumin conjugates: Normal human blood was spiked with human leukemia HL-60 cells ($10^7$/ml) and then incubated with fluorescent and Se(0)-albumin conjugates for 90 minutes. The protein source was. Flow cytometry was used to identify cells that had internalized the fluorescent conjugates.

Shelf Life of Fluorescent and Cytotoxic Photoproduct-Protein Conjugates: To assess the shelf life of fluorescent and cytotoxic conjugates, a large volume of MC54-derived conjugates was aliquoted into 2-ml plastic vials. One set of vials was stored at room temperature, one set at 5° C., one set at –20° C., and one set at –80° C. Aliquots from each set were retrieved after 1 day, 1 week, 1 month, 3 months, and 6 months, and assayed for fluorescence intensity and cytotoxic activity. In vitro clonal assays of L1210/L-PAM1 leukemia cells were used to assess cytotoxic activity.

Comparison of cytotoxic activities of Se(0)-protein conjugates produced by various light source: Selenomerocyanine photosensitizer MC54 was added from a concentrated stock solution in ethanol to alpha-medium containing 12% FCS. The mixture was exposed to cool white fluorescent light (fluence rate: 27 W/m$^2$), an identical cool white fluorescent light source fitted with a yellow acrylic filter, or an orange LED light source (peak emission at 574 nm). The medium was then used to culture murine L1210 leukemia cells and the survival rate of the leukemia cells was determined.

Effect of various light sources on generation of fluorescent conjugates: Selenomerocyanine photosensitizer MC54 was added from a concentrated stock solution in ethanol to solution of bovine serum albumin (1.75 mg/ml) in 10 mM HEPES buffer pH 7.4 to a final concentration of 20 µM and exposed to cool white fluorescent light or an orange LED light source. Small aliquots were removed at various time intervals (10 minutes to 24 hours, diluted 30-fold with HEPES buffer, and analyzed with a Hitachi F 4500 fluorescence spectrophotometer using an excitation wavelength of 490 nm. Fluorescence emission peak heights were recorded at 520 nm.

Results

Figure 18A:
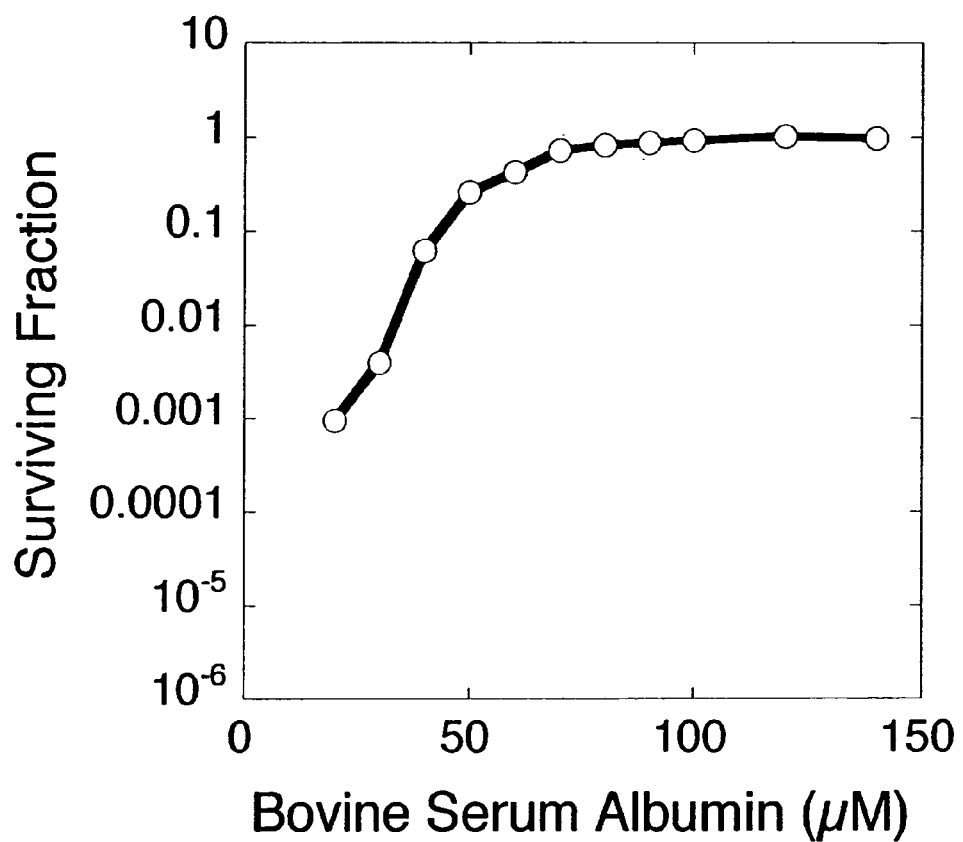
FIG. 18 shows the effect of excess native bovine serum albumin on the cytotoxic effect of Se(0)-protein conjugates (a) and the binding/uptake of fluorescent photoproduct-albumin conjugates (b) using L1210 leukemia cells. The protein source was fetal bovine serum and the Se(0) concentration was 26 µM.
Figure 18B:
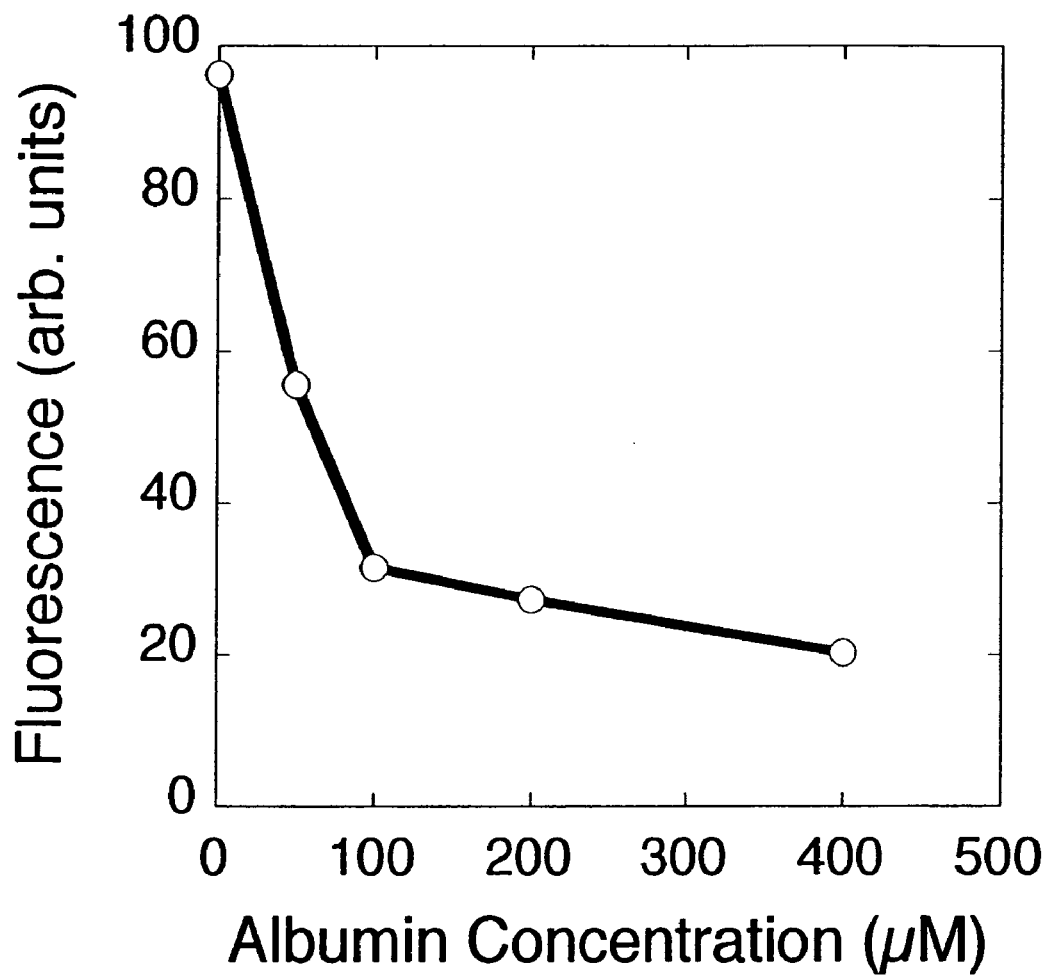
Figure 19:
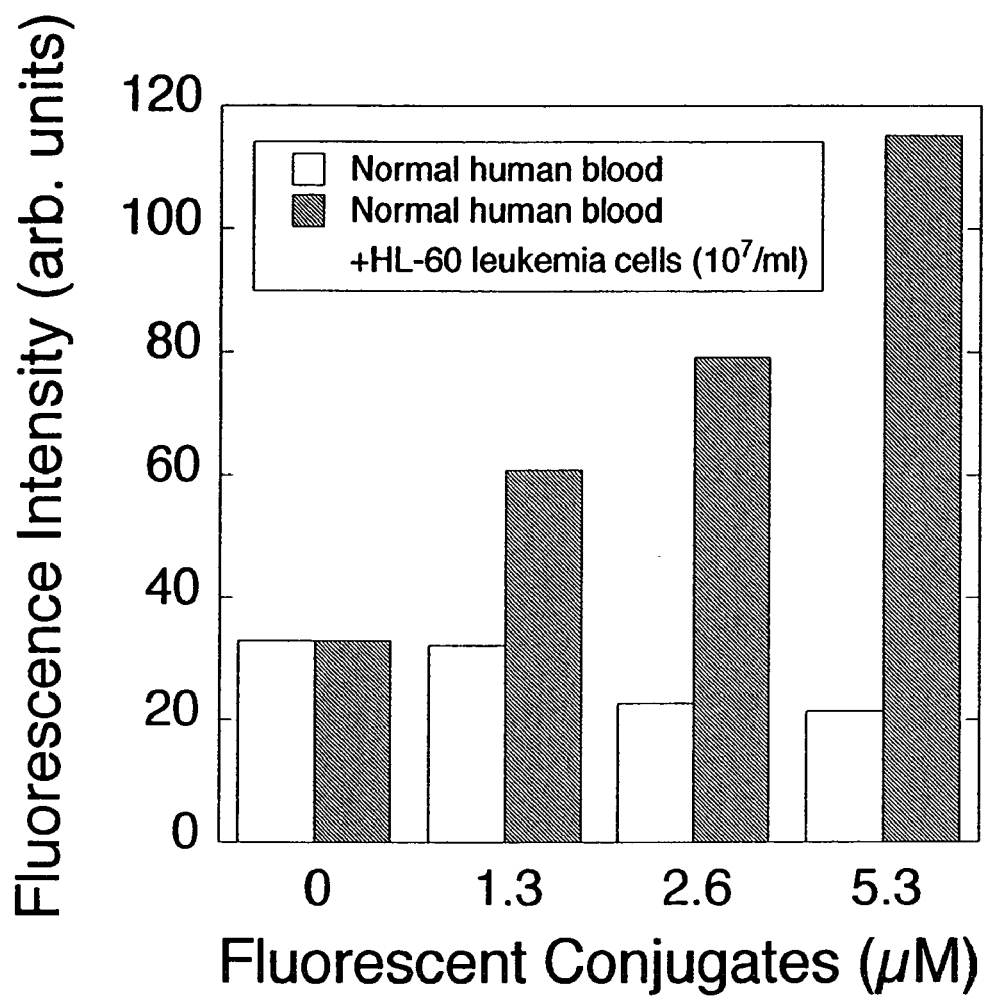
FIG. 19 shows preferential uptake of fluorescent photoproduct-albumin (bovine serum albumin) conjugates by normal human blood that had been spiked ($10^7$/ml) with HL-60 human leukemia cells. The cells were incubated with photoproduct-albumin conjugates for 90 minutes. Assay was by flow cytometer.

Effect of native albumin on cytotoxicity of Se(0)-albumin conjugates: Excess native albumin interfered with the uptake of photoproduct-albumin conjugates and protected cells against the cytotoxic effects of Se(0)-albumin conjugates (FIGS. 18a and 18b). However, the albumin concentration of whole blood was not sufficient to prevent the preferential binding and uptake of conjugates by leukemia cells (FIG. 19).

Figure 16:
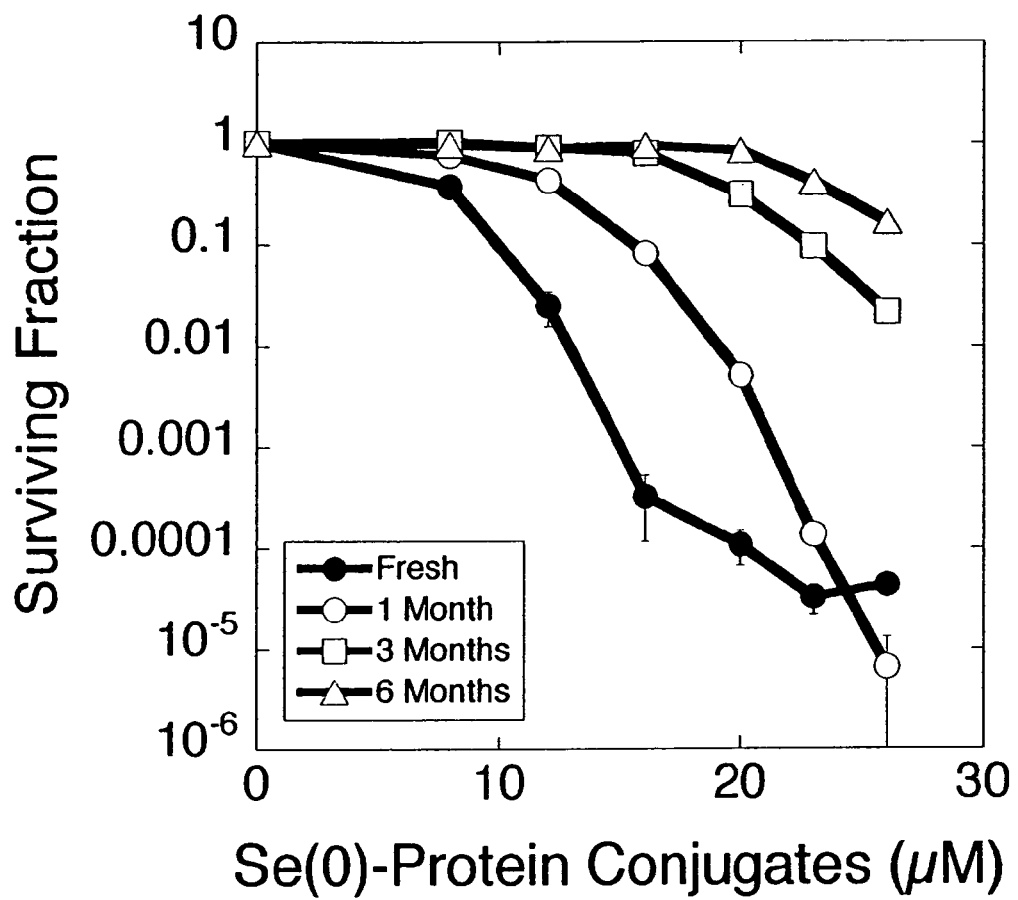
FIG. 16 shows cytotoxic activity of Se(0)-protein conjugates after storage at −20° C. The protein source was fetal bovine serum. L1210/L-PAM1 cells were treated with Se(0)-protein conjugates for one hour to assess the cytotoxic activity of the conjugates. The data points are means of 4 plates±SE.
Figure 17:
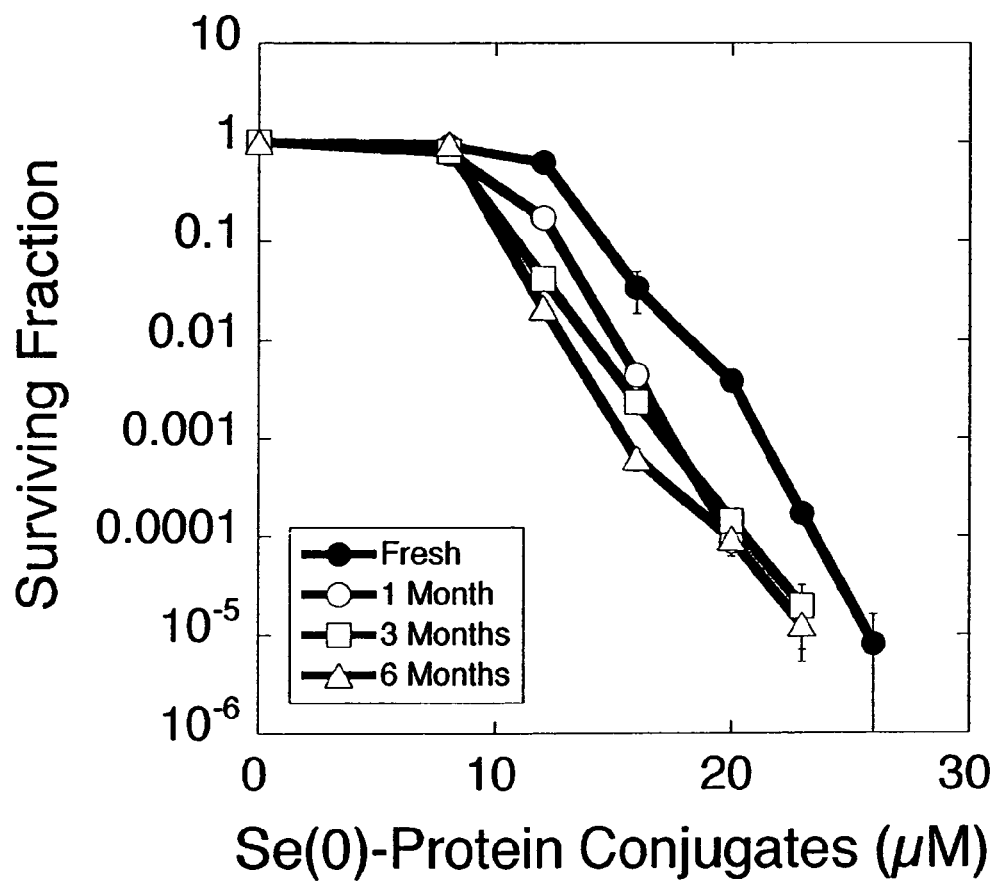
FIG. 17 shows cytotoxic activity of Se(0)-protein conjugates after storage at −80° C. The protein source was fetal bovine serum. L1210/L-PAM1 cells were treated with Se(0)-protein conjugates for one hour to assess the cytotoxic activity of the conjugates. The data points are means of 4 plates±SE.

Effects of storage and light source on fluorescence and toxicity of fluorescent and toxic conjugates: Fluorescent conjugates were stable for 6 months regardless of storage temperature. The cytotoxic activity was stable for 6 months if conjugates were stored at –80° C. (FIG. 17). Samples that were stored at room temperature, at 5° C. or at –20° C. showed a gradual loss of cytotoxic activity (see, e.g., FIG. 16). In samples that had become inactive, we noticed macroscopic precipitates of elemental selenium. This suggested that the originally very small colloidal Se(0) particles had aggregated into larger particles.

Figure 20:
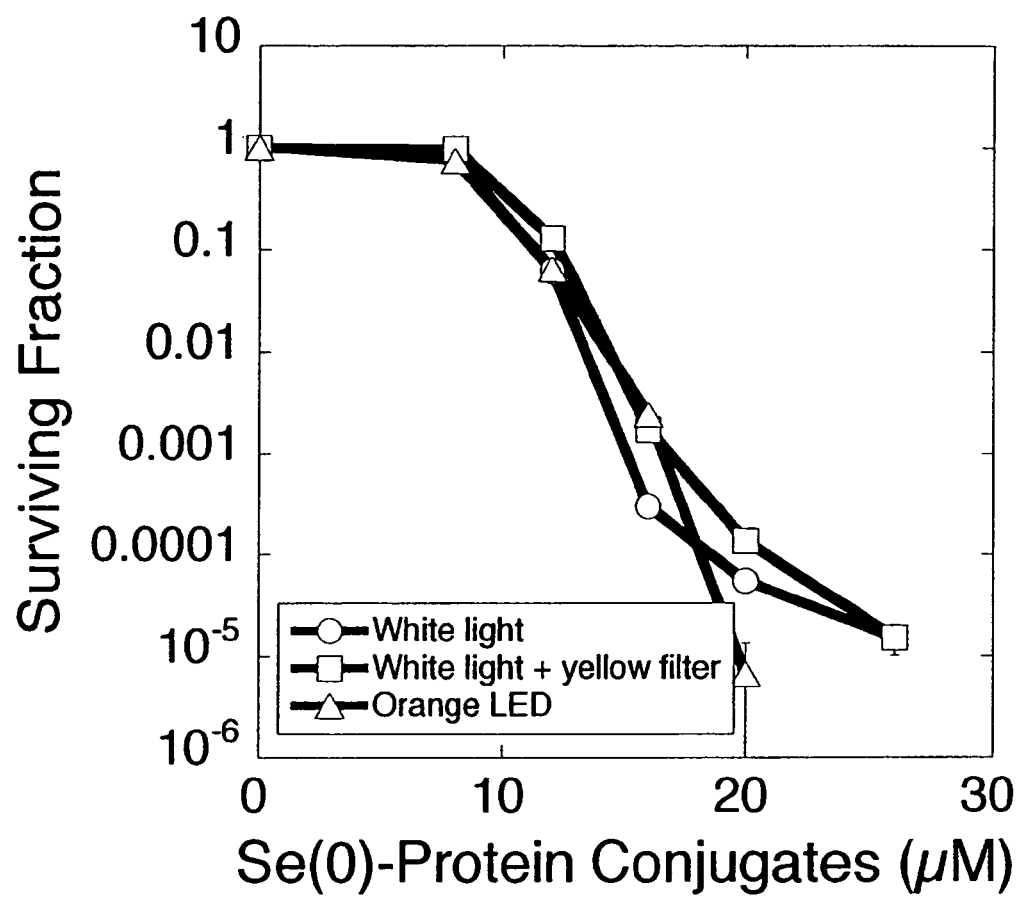
FIG. 20 shows that the light source has little or no influence on cytotoxic activity of Se(0)-protein conjugates. The study was conducted with L1210 leukemia cells. The protein source was fetal bovine serum, and the illumination time for forming Se(0)-protein conjugates was 60 minutes.
Figure 21:
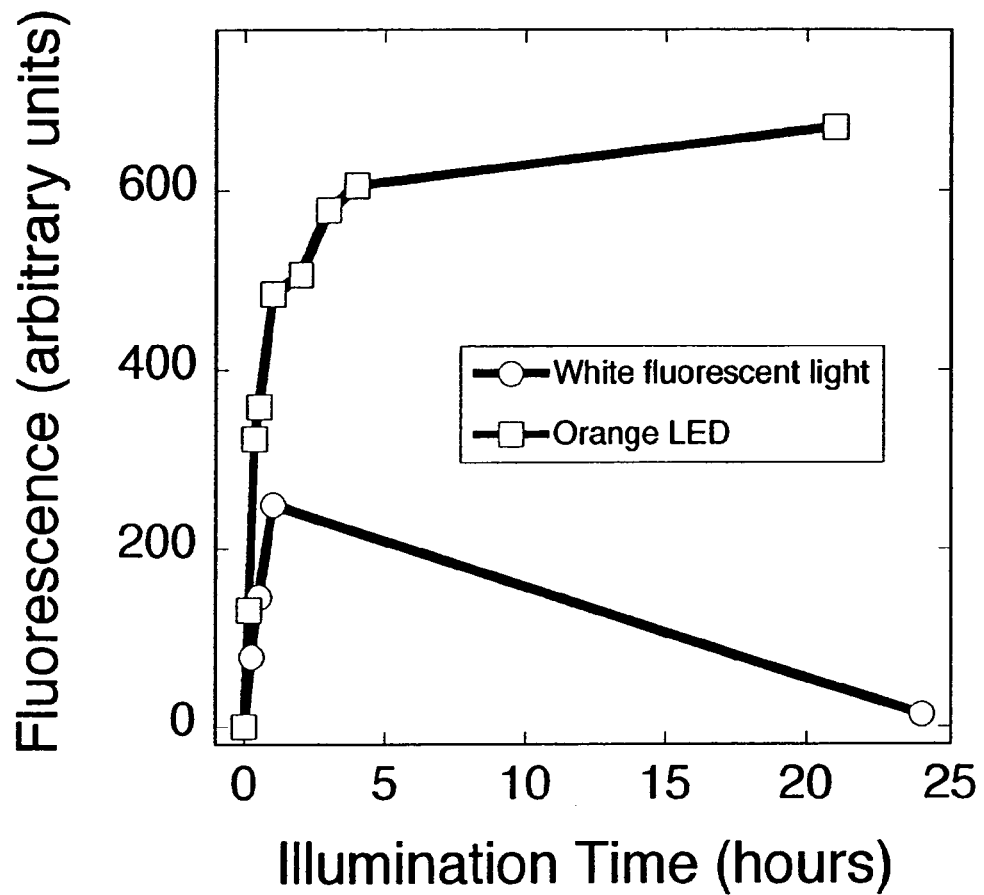
FIG. 21 shows the effect of light source on the generation of fluorescent photoproduct-albumin conjugates.

Cytotoxic activity of the Se(0)-protein conjugates was very similar regardless of the light source used to generate them (FIG. 20). The orange LED light source, however, was preferable for the generation of fluorescent conjugates (FIG. 21).

For clinical applications, one alternative to having stable Se(0)-protein conjugates would be to have a user-friendly light source that generates individual doses of cytotoxic conjugates immediately before use. We developed a small prototype LED light source with independently switched 612 and 574 nm LEDs. Both sets of LEDs photobleached MC54 very effectively. One benefit of the LED light source was that we could completely bleach the original dye and the transient chromophore photoproduct (MC47) without adversely affecting the fluorescence yield of photoproduct-albumin conjugates. As a result, the fluorescence yield of conjugates was about 200% higher than the fluorescence yield of conjugates prepared in white-light boxes. Having the capacity to prepare high-intensity green-fluorescent conjugates that were completely free of original (red-fluorescent) dye and of (orange-fluorescent) photoproduct (MC47) proved very useful for diagnostic studies that involved multiple fluorescent probes.

Acute Systemic Toxicity of Photoproduct-Protein Conjugates in Mice: In an initial acute toxicity study, groups of 5 female B6D2F1 mice were injected intraperitoneally with photoproduct-protein conjugates. The photoproduct-protein conjugates were generated by photobleaching the selenomerocyanine MC54 (26 µM) in the presence of an equimolar concentration of bovine serum albumin. Group 1 received one 1-ml intraperitoneal injection of this conjugate. Groups 2 through 5 received the same injection of conjugates on 2, 3, 4, or 5 consecutive days, respectively. All animals survived. None of the animals showed signs of acute or chronic toxicity.

The second toxicity experiment used conjugates that had been prepared with a dye-to-protein ratio of 5:1. Since MC54 was added from stock solutions in ethanol, the mice of the second series were exposed to 5-fold higher doses of ethanol. All mice showed signs of acute alcohol toxicity but no signs of toxicity attributable to Se(0)-protein conjugates.

Interactions of Cytotoxic Se(0)-Protein Conjugates with Ionizing Radiation and Standard Chemotherapeutic Agents: The objective of this study was to determine if Se(0)-protein conjugates showed evidence of synergistic antitumor activity when used in combination with ionizing radiation or standard cytotoxic drugs. Typically, 5 or 6 doses of radiation or a drug were used in combination with 1 or 2 concentrations of conjugates. Alternatively, 5 or 6 doses of conjugates were used in combination with one or two doses of a drug. Depending on the combination, the two agents were applied either sequentially or simultaneously. Drugs included melphalan, amifostine, cisplatin, edelfosine (ET-18-OCH$_3$), 4-hydroperoxy-cyclophosphamide (4-HC), arsenic (III) oxide, amphotericin B, and buthionine sulfoximine. For each combination, two or more target cells were selected from the following panel of tumor cell lines: L1210 and HL-60/ADR leukemia cells, PC3 and DU145 prostate cancer cells, H69 lung cancer cells, Mm5MT, MDA-MB-23 1, MDA-MB-435 and C1271 breast cancer cells, and SK-ES-1 Ewing's sarcoma cells.

Figure 22:
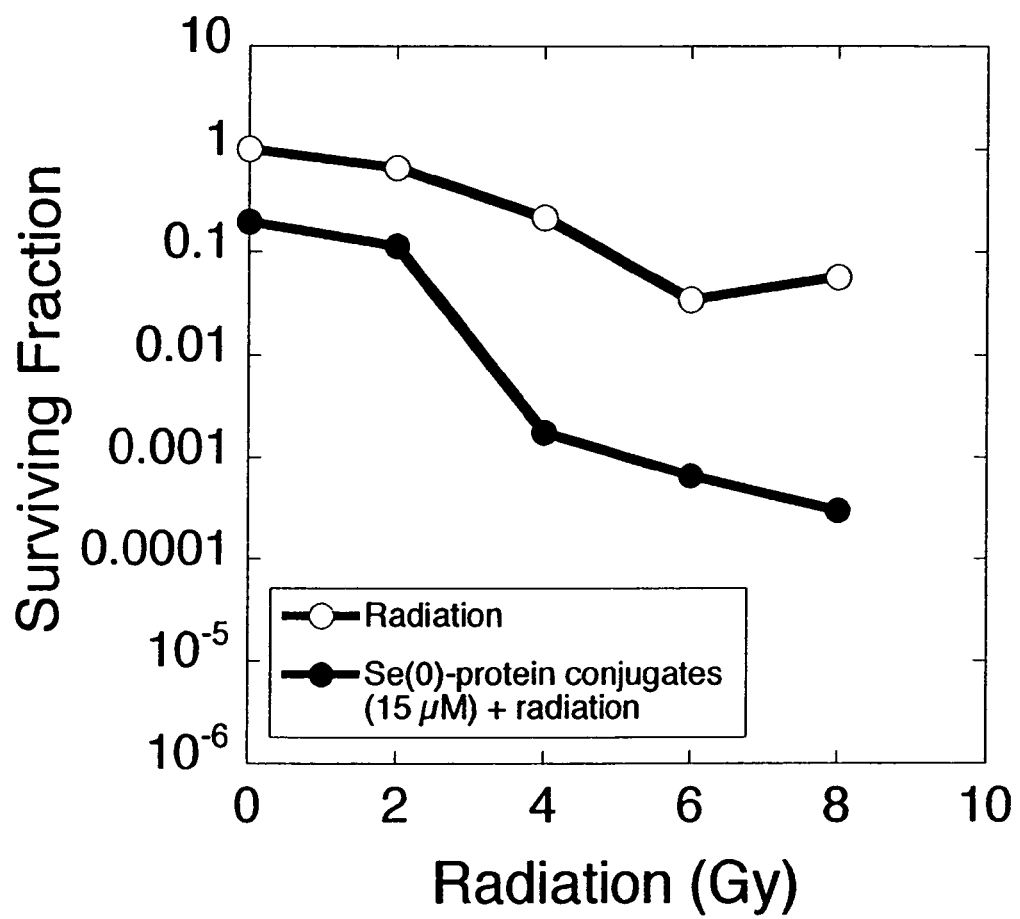
FIG. 22 shows depletion of L1210 leukemia cells by sequential exposure to Se(0)-protein conjugates and ionizing radiation. The conjugate concentration was 15 µM. The protein source was fetal bovine serum, and the data points are means of 4 plates±SE.
Figure 23:
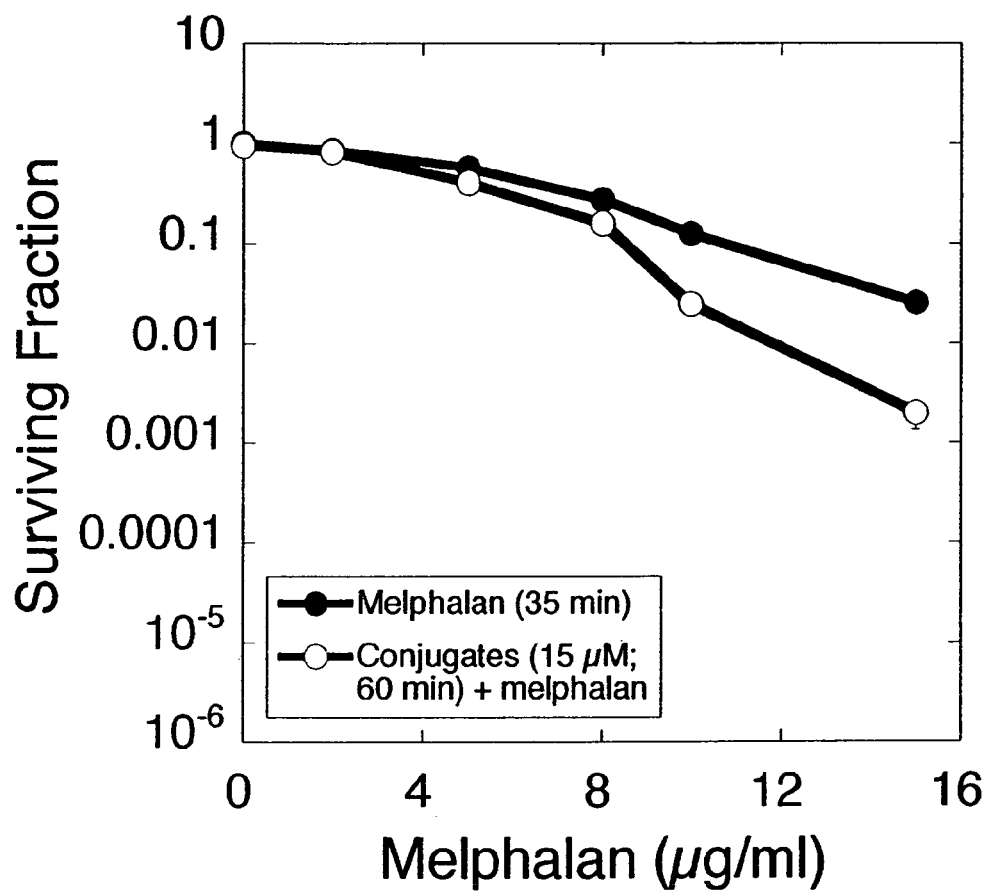
FIG. 23 shows inactivation of MDA-MB-435 human breast cancer cells by Se(0)-protein conjugates and melphalan. Cells were first exposed to conjugates (15 µM,) for 1 hour and then to melphalan for 35 minutes. The protein source was fetal bovine serum and the data points are means of 4 plates±SE.
Figure 24:
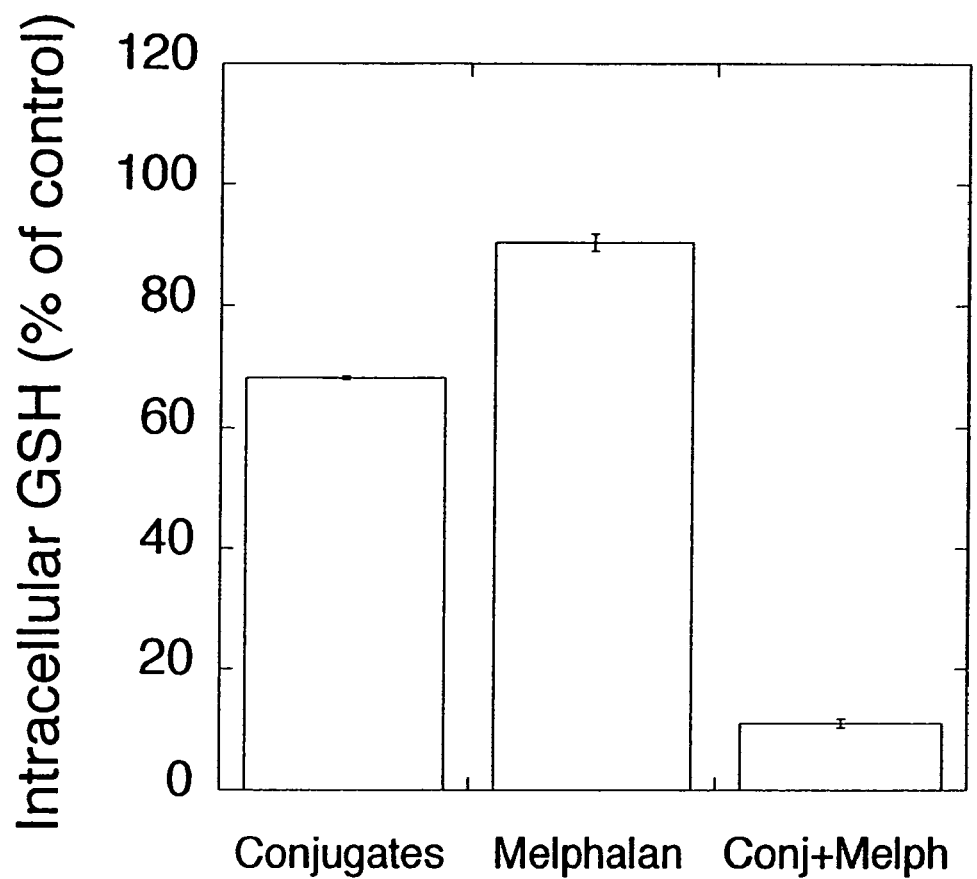
FIG. 24 shows synergistic depletion of glutathione in L1 210 leukemia cells by sequential exposure to Se(0)-protein conjugates (15 µM, 60 minutes) and melphalan (500 µM, 35 minutes). The protein source was fetal bovine serum and the data points are means of 4 plates±SE.

Pretreatment with Se(0)-protein conjugates sensitized tumor cells to melphalan and ionizing radiation (FIGS. 22 and 23). Combinations of radiation and Se(0)-protein conjugates were more effective in L1210 leukemia and PC3 prostate cancer than in DU145 prostate cancer cells. Conjugates and melphalan synergistically depleted intracellular GSH (FIG. 24). Combinations of Se(0)-protein conjugates and 4-HC appeared to have an additive antitumor effect.

Figure 25:
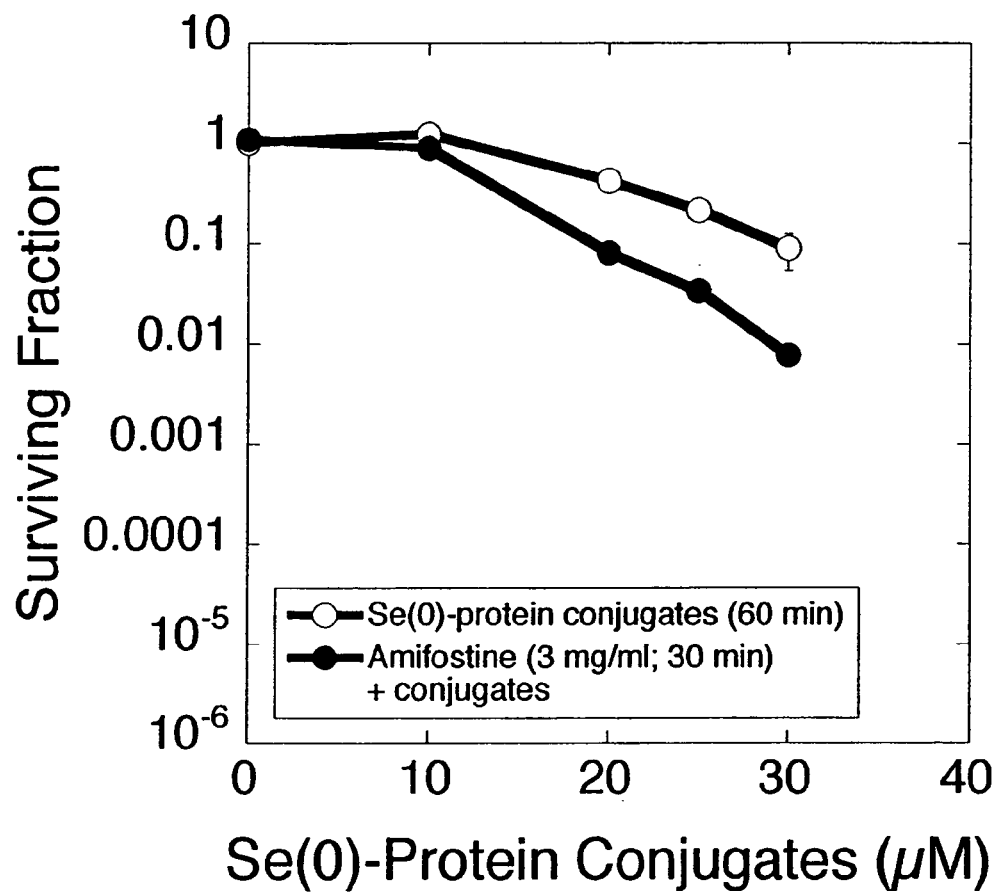
FIG. 25 shows that pretreatment with a nontoxic dose (3 mg/ml) of amifostine for 30 minutes potentiates inactivation of MDA-MB 435 human breast cancer cells by Se(0)-protein conjugates. The protein source was fetal bovine serum. Data points represent mean colony counts of 4 culture dishes±SE.
Figure 26:
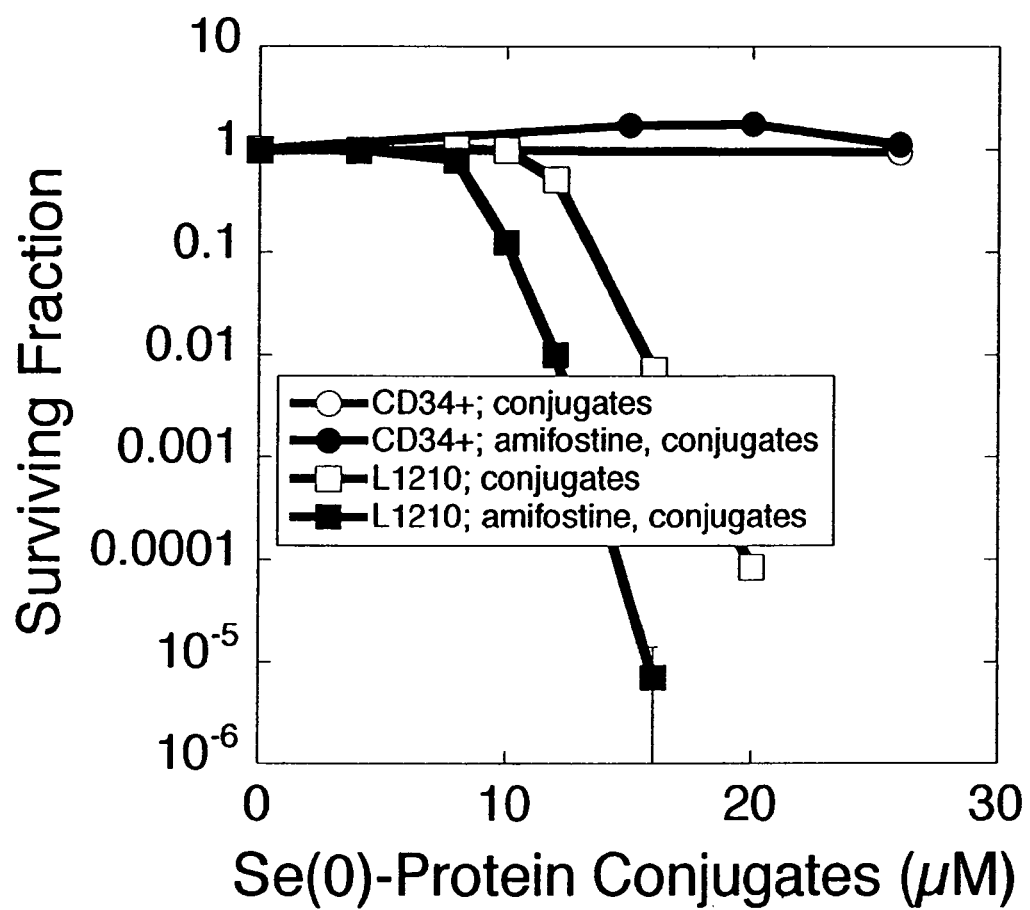
FIG. 26 shows that pretreatment with amifostine potentiates killing of leukemia cells by Se(0)-protein conjugates without compromising survival of normal murine CD34-positive stem cells. L1210 murine leukemia cells and normal murine bone marrow cells were incubated with amifostine (3 mg/ml) for 30 min at 37° C., washed free of excess Amifostine, and then exposed to graded concentrations of Se(0)-protein conjugates for 60 min at 37° C. The survival of L1210 cells was determined by in vitro clonal assay. CD34-positive cells were identified with a FITC-conjugated antibody. FITC-positive cells were enumerated with a flow cytometer. Conjugates were prepared with fetal bovine serum and MC56. We used MC56 (which generates nonfluorescent conjugates) instead of MC54 because we had to avoid interference with the FITC-conjugated antibody.

A brief (30 min) pretreatment with a nontoxic (3 mg/ml) concentration of amifostine sensitized tumor cells to cytotoxic conjugates (FIGS. 25 and 26). The effect was more pronounced in L1210 leukemia and MDA-MB-435 breast cancer than in DU145 prostate cancer cells. FIG. 26 shows that pretreatment with amifostine potentiated killing of L1210 murine leukemia cells by Se(0)-protein conjugates without compromising survival of normal murine CD34-positive hematopoietic stem cells. The complete recovery of CD34-positive cells indicates minimal damage or no damage to the hematopoietic stem cell compartment. Resistance of CD34-positive stem cells to combination therapy with amifostine and cytotoxic conjugates has been confirmed with bone marrow cells of human origin. Binding/uptake experiments indicate that the enhanced sensitivity of amifostine-treated tumor cells to cytotoxic conjugates is the result of enhanced conjugate uptake.

Figure 27:
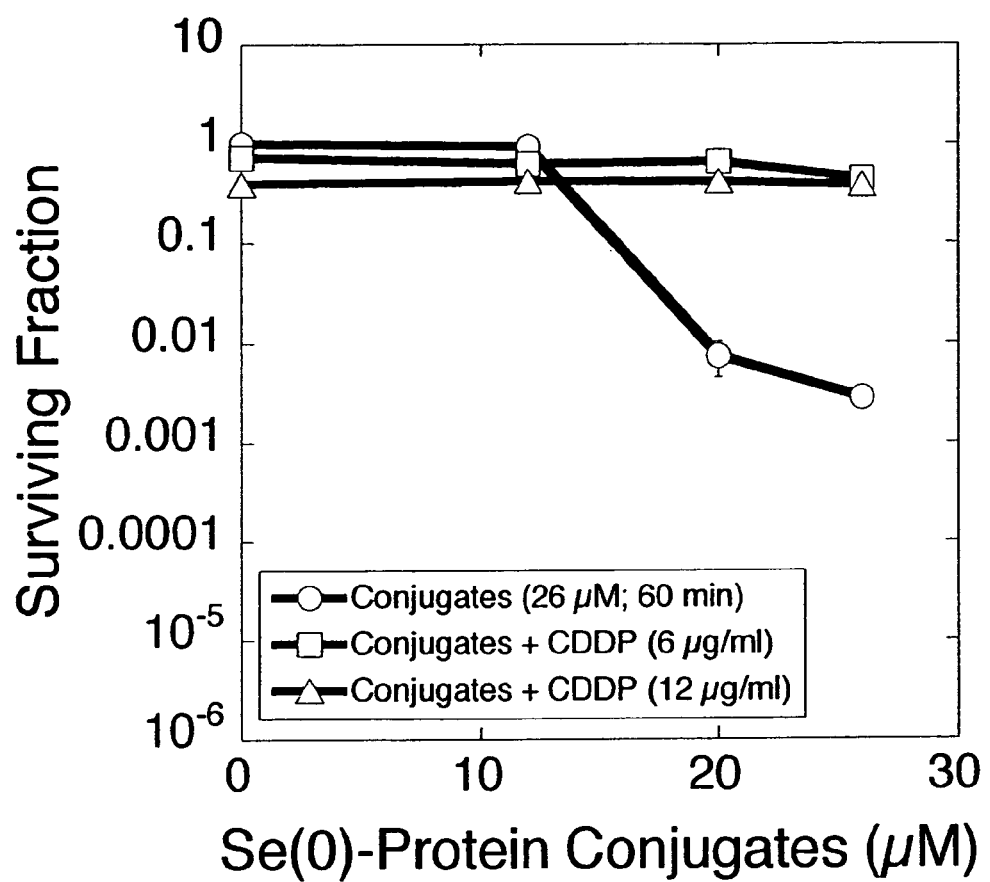
FIG. 27 shows that simultaneously applied cisplatin has antagonistic effect on cytotoxic action of Se(0)-protein conjugates. The study was conducted with DU145 human prostate cancer cells. The protein source was fetal bovine serum, and the data points are means of 4 plates±SE.

Low doses (6–12 µg/ml) of cisplatin (CDDP) applied simultaneously with Se(0)-protein conjugates completely neutralized the cytotoxic effects of conjugates on DU145 prostate cells (FIG. 27). Cisplatin did not appear to interfere significantly with the binding/uptake of fluorescent photoproduct-albumin conjugates by moderately sensitive prostate or breast cancer cells. When experiments were extended to highly sensitive L1210 and L1210/L-PAM1 leukemia cells and to normal granulocyte/macrophage progenitors, the antagonistic effect of CDDP was confirmed. However, unlike in solid tumor cells, conjugate uptake was significantly reduced in leukemia cells. As a result of the reduced conjugate uptake, intracellular glutathione (GSH) levels (determined with the fluorescent probe monochlorobimane) were only minimally reduced in CDDP-treated cells. When cells were sequentially exposed to cisplatin and Se(0)-protein conjugates, the antitumor effect of the two agents appeared to be additive in DU145 and PC3 prostate cancer cells. Combinations of edelfosine (50 µg/ml; 60 min) and Se(0)-protein conjugates were moderately effective if cells were exposed to edelfosine first. Using the two agents in reverse order or simultaneously produced inferior results. Breast cancer cells responded better to edelfosine/conjugate combinations than prostate cancer cells. Pretreatment with buthionine sulfoximine (0.5 mM; 20 hours) improved the response of DU145 prostate cancer cells to conjugates but had little or no effect on the response of PC3 prostate and MDA-MB-435 breast cancer cells.

REFERENCES

Ahmad S, Okine L, Le B, Najarian P, Vistica D T: Elevation of glutathione in phenylalanine mustard-resistant murine L1210 leukemia cells. J Biol Chem 262: 15048–15053, 1987.

Davis R L, Spallholz J E, Pence B C: Inhibition of selenite-induced cytotoxicity and apoptosis in human colonic carcinoma (HT-29) cells by copper. Nutrition & Cancer 32: 181–189, 1998.

Günther W H H, Searle R, Sieber F: Photosensitizing merocyanine dyes based on selenobarbituric acid. Phosphorus, Sulfur, and Silicon 67: 417–424, 1992.

Hug H, Los M, Hirt W, Debatin K-M: Rhodamine 110-linked amino acids and peptides as substrates to measure caspase activity upon apoptosis induction in intact cells. Biochem 38: 13906–13911, 1999.

Kasahara K, Fujiwara Y, Nishio K, Ohmori T, Sugimoto Y, Komoya K, Matsuda T, Sajijo N: Metallothionein content correlates with the sensitivity of human small cell lung cancer cell lines to cisplatin. Cancer Res 51: 3237–3242, 1991.

Krieg M, Bilitz J M, Traul D L and Sieber F: Photosensitizing oxonol dyes with antineoplastic activity. Cancer Res Ther Contr 4: 163–172, 1995.

Krishnamachary N, Center M S: The MRP gene associated with a non-P-glycoprotein multidrug resistance encodes a 190-kDa membrane bound glycoprotein. Cancer Res 53: 3658–3661, 1993.

Lin Y, Spallholz J E: Generation of reactive oxygen species from the reaction of selenium compounds with thiols and mammary tumor cells. Biochem Pharmacol 45: 429–437, 1993.

Los M, Walczak H, Schulze-Osthoff K, Reed J C: Fluorogenic substrates as detectors of caspase activity during natural killer cell-induced apoptosis. Methods Mol Biol 121: 155–162, 2000.

Ohmori T, Morikage T, Sugimoto Y, Fujiwara Y, Kasahara K, Nishio K, Ohta S, Sasaki Y, Takahashi T, Saijo N: The mechanism of the difference in cellular uptake of platinum derivatives in non-small cell lung cancer cell line (PC-14) and its cisplatin-resistant subline (PC-14/CDDP). Jap J Cancer Res 84: 83–92, 1993.

Oleinick N L, Morris R L, Belichenko I: The role of apoptosis in response to photodynamic therapy: what, where, why, and how. Photochem Photobiol Sci 1: 1–21, 2002.

Oyama Y, Hayashi A, Ueba T, Maekawa K: characterization of 2',7'-dichlorofluorescin fluorescence in dissociated mammalian brain neurons: estimation of intracellular content of hydrogen peroxide. Brain Res 635: 113–117, 1994.

Sieber F, Spivak J L, Sutcliffe A M: Selective killing of leukemic cells by merocyanine 540-mediated photosensitization. Proc Natl Acad Sci USA 81: 7584–7587, 1984.

Sieber F, Stuart R K, Rowley S D, Sharkis S J, Sensenbrenner L L: Dye-mediated photolysis of normal and neoplastic hematopoietic cells. Leukemia Res 11: 43–49, 1987.

Stewart M S, Davis R L, Walsh L P, Pence B C: Induction of differentiation and apoptosis by sodium selenite in human colonic carcinoma cells (HT29). Cancer Letters 117: 35–40, 1997.

Trayner I D, Rayner A P, Freeman G E, Farzaneh F: Quantitative multiwell myeloid differentiation assay using dichlorodihydrofluorescein diacetate (H2DCF-DA) or dihydrorhodamine 123 (H2R123). J Imm Meth 186: 275–284, 1995.

The present invention is not intended to be limited to the foregoing examples, but encompasses all such modifications and variations as come within the scope of the appended claims.

We claim:

1. A composition comprising:
   elemental selenium (Se(0)) particles having a diameter of 0.4 to 1 nanometer; and a
   pharmaceutically acceptable delivering medium.

2. The composition of claim 1, further comprising:
   a carrier molecule that can be internalized by a living cell wherein the carrier molecule forms a conjugate with one or more Se(0) particles.

3. The composition of claim 2, wherein the carrier molecule is selected from the group consisting of proteins, glycoproteins and lipoproteins.

4. The composition of claim 2, wherein the carrier molecule is selected from the group consisting of albumin, high density lipoprotein, low density lipoprotein and very low density lipoprotein.

5. The composition of claim 1, wherein the elemental selenium (Se(0)) particles can form a Se(0) colloid in a dispersion medium.

6. A composition comprising:
   elemental selenium (Se(0)) particles having a diameter of 0.4 to 1 nanometer;
   a target cell-specific carrier molecule that can be internalized by a living cell wherein the carrier molecule forms a conjugate with one or more Se(0) particles; and
   a pharmaceutically acceptable delivering medium.

7. A pharmaceutical composition comprising:
   elemental selenium (Se(0)) particles having a diameter of 0.4 to 1 nanometer;
   a target cell-specific carrier molecule that can be internalized by a living target cell wherein the carrier molecule is albumin and forms a conjugate with one or more Se(0) particles; and
   a pharmaceutically acceptable delivering medium.

8. A composition comprising:
   elemental selenium (Se(0)) particles having a diameter of 0.4 to 1 nanometer;
   a target cell-specific carrier molecule that can be internalized by a living target cell selected from the group consisting of a cancer cell, an immune cell responsible for an autoimmune disorder, an alloreactive lymphocyte responsible for graft-versus-host disease or a rejection reaction, a parasite and a parasitized blood cell, wherein the carrier molecule forms a conjugate with one or more Se(0) particles; and
   a pharmaceutically acceptable delivering medium.

9. The composition of claim 8, wherein the living target cell is a cancer cell.

10. A method for generating Se(0) comprising the steps of:
    providing a photosensitizing selone dye;
    exposing the dye to light of a suitable wavelength in the presence of molecular oxygen; and
    purifying Se(0).

11. The method of claim 10, wherein the photosensitizing selone dye is selected from the group consisting of a selenomerocyanine dye and a selenooxonol dye.

12. The method of claim 11, wherein the selenomerocyanine dye is selected from the group consisting of MC54, MC55, MC56 and MC57.

13. The method of claim 10, wherein Se(0) is colloidal Se(0).

14. The method of claim 10, wherein the light of suitable wavelength is generated by light-emitting diodes (LED).

15. A method for treating a human or nonhuman subject having cancer comprising the step of:
    administering a composition that comprises a pharmaceutically effective amount of Se(0) particles having a diameter of 0.4 to 1 nanometers and a carrier molecule that can be internalized by a cancer cell, wherein the carrier molecule is albumin, and forms a conjugate with one or more Se(0) particles, to the human or nonhuman subject.

16. The method of claim 15, wherein the Se(0) particles can form a Se(0) colloid in a dispersion medium.

17. A method for sensitizing a cell to a cytotoxic agent wherein the cell is resistant to the cytotoxic agent due to the presence of intracellular glutathione, the method comprising of:
    treating the cell, or a human or nonhuman subject having the cell, with a composition that comprises Se(0) particles having a diameter of 0.4 to 1 nanometers and a carrier molecule that can be internalized by the cell and forms a conjugate with one or more Se(0) particles, wherein the cell becomes susceptible to the killing by an otherwise ineffective amount of the cytotoxic agent.

* * * * *

UNITED STATES PATENT AND TRADEMARK OFFICE
CERTIFICATE OF CORRECTION

PATENT NO.       : 7,205,002 B2                                    Page 1 of 1
APPLICATION NO.  : 10/701870
DATED            : April 17, 2007
INVENTOR(S)      : Fritz Sieber et al.

It is certified that error appears in the above-identified patent and that said Letters Patent is hereby corrected as shown below:

Col. 4, Lines 40-41 "L1 210" should be -- L1210 --

Col. 15, Line 4 "Comjugates" should be -- Conjugates --

Col. 15, Line 30 "$\geqq$ 4 log" should be -- $\geq$ 4 log --

Col. 19, Line 28 "of $\geqq$ 5 log" should be -- of $\geq$ 5 log --

Col. 23, Line 20 "MDA-MB-23 1," should be -- MDA-MB-231, --

Signed and Sealed this

Twenty-fifth Day of March, 2008

JON W. DUDAS
*Director of the United States Patent and Trademark Office*